United States Patent
Shi et al.

(10) Patent No.: US 11,590,237 B2
(45) Date of Patent: Feb. 28, 2023

(54) PHARMACEUTICAL FORMULATION COMPRISING INCRETIN-INSULIN CONJUGATES

(71) Applicants: Merck Sharp & Dohme Corp., Rahway, NJ (US); Shuai Shi, Whippany, NJ (US); Valentyn Antochshuk, Cranford, NJ (US)

(72) Inventors: Shuai Shi, Whippany, NJ (US); Valentyn Antochshuk, Cranford, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 48 days.

(21) Appl. No.: 16/607,453

(22) PCT Filed: May 14, 2018

(86) PCT No.: PCT/US2018/032487
§ 371 (c)(1),
(2) Date: Oct. 23, 2019

(87) PCT Pub. No.: WO2018/213151
PCT Pub. Date: Nov. 22, 2018

(65) Prior Publication Data
US 2020/0069809 A1 Mar. 5, 2020

Related U.S. Application Data
(60) Provisional application No. 62/507,964, filed on May 18, 2017.

(51) Int. Cl.
| | |
|---|---|
| A61K 38/28 | (2006.01) |
| A61K 47/64 | (2017.01) |
| A61P 3/10 | (2006.01) |
| A61K 9/00 | (2006.01) |
| A61K 9/08 | (2006.01) |
| A61K 38/26 | (2006.01) |
| A61K 47/02 | (2006.01) |
| A61K 47/10 | (2017.01) |
| A61K 47/18 | (2017.01) |

(52) U.S. Cl.
CPC ............ *A61K 47/64* (2017.08); *A61K 9/0019* (2013.01); *A61K 9/08* (2013.01); *A61K 38/26* (2013.01); *A61K 38/28* (2013.01); *A61K 47/02* (2013.01); *A61K 47/10* (2013.01); *A61K 47/183* (2013.01); *A61P 3/10* (2018.01)

(58) Field of Classification Search
CPC ............................. A61K 47/64; A61K 47/183
See application file for complete search history.

(56) References Cited

U.S. PATENT DOCUMENTS

| | | | | |
|---|---|---|---|---|
| 5,833,669 A | * | 11/1998 | Wyrick | A61M 5/31595 604/234 |
| 6,630,348 B1 | | 10/2003 | Lee et al. | |
| 2011/0046052 A1 | * | 2/2011 | Yang | A61K 47/08 546/25 |
| 2013/0058958 A1 | * | 3/2013 | Bowen | C07K 16/2812 424/172.1 |
| 2013/0202620 A1 | * | 8/2013 | Osslund | A61K 39/3955 424/172.1 |
| 2015/0258207 A1 | | 9/2015 | Rau et al. | |
| 2020/0299668 A1 | * | 9/2020 | Wang | C12N 9/6432 |

FOREIGN PATENT DOCUMENTS

| | | |
|---|---|---|
| WO | 9634882 A1 | 11/1996 |
| WO | WO2008022015 A2 | 2/2008 |
| WO | 2009058734 A1 | 5/2009 |
| WO | 2009148089 A1 | 12/2009 |
| WO | 2009155258 A2 | 12/2009 |
| WO | 2010071807 A1 | 6/2010 |
| WO | 2010080607 A1 | 7/2010 |
| WO | 2010080609 A1 | 7/2010 |
| WO | 2011012718 A1 | 2/2011 |
| WO | 2011094337 A1 | 8/2011 |
| WO | 2011159882 A2 | 12/2011 |
| WO | 2011159895 A2 | 12/2011 |
| WO | 2011163473 A1 | 12/2011 |
| WO | 2014158900 A1 | 10/2014 |
| WO | 2016049190 A1 | 3/2016 |

(Continued)

OTHER PUBLICATIONS

Baynes, B.M. et al., Role of arginine in the stabilization of proteins against aggregation, Biochemistry, 2005, 4919-4925, 44(12).
Alam, Parver et al., Ascorbic acid inhibits human insulin aggregation and protects against amyloid induced cytotoxicity, Archives of Biochemistry and Biophysics, 2017, 54-62, 621.
Arnolds, Sabine et al., Further Improvement in Postprandial Glucose Control With Addition of Exenatide or Sitagliptin to Combination Therapy With Insulin Glargine and Metformin, Diabetes Care, 2010, 1509-1515, 33.
Christensen, Mikkel et al., Glucose-Dependent Insulinotropic Polypeptide Augments Glucagon Responses to Hypoglycemia in Type 1 Diabetes, Diabetes, 2015, 72-78, 64.

(Continued)

*Primary Examiner* — Gyan Chandra
(74) *Attorney, Agent, or Firm* — Baerbel R. Brown; Catherine D. Fitch

(57) ABSTRACT

This disclosure relates to stable aqueous pharmaceutical formulations comprising a therapeutically effective amount of an incretin-insulin conjugate as well as methods of using the same, and aqueous pharmaceutical formulations containing an incretin-insulin conjugate which are stable and which provide a protracted pharmacodynamics profile, which include L-arginine HCl and phenol (or m-cresol) as stabilizing agents. The invention also provide a method of treating a patient or individual having a metabolic disease, comprising administering to the patient or individual an effective amount of any of the aqueous pharmaceutical formulations described herein.

14 Claims, 7 Drawing Sheets

Specification includes a Sequence Listing.

(56) References Cited

FOREIGN PATENT DOCUMENTS

| WO | WO2016111971 A1 | 7/2016 |
| WO | 2017189342 A1 | 11/2017 |

OTHER PUBLICATIONS

Christensen, Mikkel et al., Glucose-dependent Insulinotropic Polypeptide: Blood Glucose Stabilizing Effects in Patients with Type 2 diabetes, J Clin Endocrinol Metab, 2014, 1-9 pages, 99:E418-426.

D.H.C. Chou et al., Glucose-responsive insulin activity by covalent modification with aliphatic phenylboronic acid conjugates, Proc. Natl. Acad. Sci., 2015, 2401-2406, 112.

Dunn, Michael F., Zinc-ligand interactions modulate assembly and stability of the insulin hexamer—a review, BioMetals, 2005, 295-303, 18.

Finan, Brian, et al., Unimolecular Dual Incretins Maximize Metabolic Benefits in Rodents, Monkeys, and Humans, Science Translational Medicine, 2013, p. 1-18, vol. 5, Issue 209.

Gault, Victor A. et al., Characterisation and giucoregulatory actions of a novel acylated form of the (Pro3)GIP receptor antagonist in type 2 diabetes, Biological Chemistry, 2007, 173-179, 388.

Gough, Stephen C.L. et al., Efficacy and safety of a fi xed-ratio combination of insulin degludec and liraglutide (IDegLira) compared with its components given alone: results of a phase 3, open-label,, Lancet Diabetes Endocrinol., 2014, 885-893, 2.

Hood Thabit et al., Coming of age: the artificial pancreas for type 1 diabetes, Diabetologia, 2016, 1795-1805, 59.

Jicheng Yu et al., Microneedle-array patches loaded with hypoxia-sensitive vesicles provide fast glucose-responsive insulin delivery, Proc. Natl. Acad. Sci. USA, 2015, 8260-8265, 112(27).

Junling Guo et al., Boronate-Phenolic Network Capsules with Dual Response to Acidic pH and Cis-Diols, Adv. Healthc Mater., 2015, 1976-1801, 112.

Lao, J et al., Effect of GLP1R/GCGR Dueal Agonist in Monkey, Diabetes, 2013, A217-A364, 62:A257.

M. Brownlee et al., A Glucose-Controlled Insulin-Delivery System: Semisynthetic Insulin Bound to Lectin, Science, 1979, 1190-1191, 206.

Nathan, Davaid M. et al., Medical Management of Hyperglycemia in Type 2 Diabetes: A Consensus Algorithm for the Initiation and Adjustment of Therapy, Diabetes Care, 2009, 193-203, 32(1).

P.E. Cryer, Hypoglycaemia: The limiting factor in the glycaemic management of Type 1 and Type 2 Diabetes, Diabetologia, 2002, 937-948, 45.

Palmer, Suetonia C. et al., Comparison of Clinical Outcomes and Adverse Events Associated With Glucose-Lowering Drugs in Patients With Type 2 Diabetes, JAMA, 2016, 313-324, 316.

Sebokova, Elena et al., Taspoglutide, an Analog of Human Glucagon-Like Peptide-1 with Enhanced Stability and in Vivo Potency, Endocrinology, 2010, 2474-2482, 151(6).

Wang, Ying et al., Transformation of Oligomers of Lipidated Peptide Induced by Change in pH, Molecular Pharmaceutics, 2015, 411-419, 12.

Widenmaier, Scott B. et al., A GIP Receptor Agonist Exhibits b-Cell Anti-Apoptotic Actions in Rat Models of Diabetes Resulting in Improved b-Cell Function and Glycemic Control, PLoS One, 2010, 1-10 pages, 5:e9590.

Xiuli Hu et al., H2O2-Responsive Vesicles Integrated with Transcutaneous Patches for Glucose-Mediated Insulin Delivery, ACS Nano, 2017, 613-620, 11.

* cited by examiner

RHI (Zinc driven hexamer)

Victoza (Micelle)

Hypothetical assembly model for triagonist

PHARMACEUTICAL FORMULATION COMPRISING INCRETIN-INSULIN CONJUGATES

CROSS-REFERENCE TO RELATED APPLICATIONS

This application is a U.S. National Phase application under 35 U.S.C. § 371 of PCT Application No. PCT/US2018/032487, filed on May 14, 2018, which claims priority from and the benefit of U.S. Provisional Application No. 62/507,964, filed May 18, 2017.

REFERENCE TO SEQUENCE LISTING SUBMITTED ELECTRONICALLY

The sequence listing of the present application is submitted electronically via EFS-Web as an ASCII formatted sequence listing with the file 24446WOPCT-SEQTXT-2MAY2018 creation date May 2, 2018, and size 19 KB. This sequence listing submitted via EFS-Web is part of the specification and is herein incorporated by reference in its entirety.

FIELD OF THE INVENTION

The present invention relates to stable aqueous pharmaceutical formulations comprising (i) a therapeutically effective amount of an incretin-insulin conjugate which comprises an incretin peptide and an insulin molecule, (ii) a buffer (iii) glycerin, (iv) phenol or m-cresol, and (v) L-arginine HCl, wherein the pharmaceutical formulation has a pH of about 6.9-7.5. In one embodiment the incretin peptide has the structure:

(SEQ ID NO: 1)
$X_1X_2X_3GX_4FTSDX_5SX_6YLDX_7X_8AAX_9X_{10}FVX_{11}WLLX_{12}X_{13}GPSSGAPPPSX_{14}$.

In one aspect, the formulation comprises the incretin-insulin conjugate, sodium phosphate dibasic, glycerin, phenol, and L-arginine hydrochloride having a pH of 7.2 Such formulations are stable and provide a protracted pharmacodynamics profile as compared to formulations which do not contain L-Arginine HCl.

BACKGROUND OF THE INVENTION

Diabetes mellitus (Type 1 and Type 2; T1DM, T2DM) is a global public health issue believed to affect 415 million individuals worldwide in 2015, with a prevalence estimated to reach 642 million by 2040. Nearly 10% of the US population is currently directly affected by the disease, and by 2050 it is estimated that 1 in 3 American adults will have diabetes. According to CDC (Center for Disease Control and Prevention) statistics, 14% of all diabetics in the US are on insulin alone, and another 13% are on a combination of insulin and oral therapy.[1]

Insulin is currently the most effective drug for the treatment of diabetes. However, many diabetics prescribed insulin do not attain clinically recommended targets for glycemic control. One of the most prominent reasons for not achieving optimal efficacy with insulin is the narrow therapeutic index (TI) between ideal glycemic control and hypoglycemic risk.[2] This narrow TI of insulin, evident in a steep slope of the dose-response, poses a significant challenge to precisely dose both rapid acting and basal insulin preparations. Excessive basal insulin creates a prolonged risk of hypoglycemia and challenging dose titrations. A consequence of this challenging dose-titration is that practitioners and patients often settle at moderate under-dosing of basal insulin, mitigating though not totally avoiding hypoglycemia and yet failing to achieve fully efficacious dosing.[3,4] Although there is on-going development in basal insulin focused mostly on optimizing flatness of pharmacokinetics (PK), such efforts do not address the narrow TI intrinsic to available insulin analogs.

A persistent risk for hypoglycemia can cause patients to be cautious with insulin dosing. A key impetus to create closed-loop insulin delivery is to establish real-time communication about ambient glucose that can inform and modulate exogenous insulin delivery.[5] Another approach to creating communication between exogenously administered insulin and a patient's blood glucose is to engineer insulin so that it will intrinsically respond to fluctuations in ambient glucose. The notion of glucose responsive insulin (GRI) was proposed nearly 40 years ago.[6] A number of attempts at creating a GRI have been reported and most of these have sought to exploit the concept of incorporating insulin into a matrix containing glucose sensitive "triggers" that affect release of insulin from a subcutaneous depot.[7-10] However, most of the aforementioned approaches have met with limited success primarily because of the challenges associated with attaining glucose modulation of insulin action across a relatively small range of ambient glucose concentrations.

Incretin-insulin conjugates, including a peptide tri-agonist, were developed to address the unmet medical need for diabetes control, in order to achieve superior HbA1C-lowering efficacy, wider therapeutic index, and significantly reduced rate of hypoglycemia. Tri-agonist incretin-insulin conjugates contain a glucagon-like peptide-1 (GLP-1), gastric inhibitory polypeptide (GIP) and recombinant human insulin in a single molecule and are promising clinical candidates for better control of blood glucose and body weight.[11] The benefits of combining insulin and a GLP-1 agonist therapy include improved efficacy and safety profiles.[12,13] Addition of a GLP-1 agonist mitigates the weight gain associated with insulin therapy by reducing the amount of insulin used to maintain glycemic control, GLP-1 agonists also independently lower body weight due to interaction with satiety centers in the central nervous system and/or delaying gastric emptying. However, GLP-1 agonists are associated with nausea and/or vomiting in up to 20% of patients which limits their dose range. Similar to GLP-1, GIP, is an incretin secreted from intestinal cells in response to ingestion of food. When administered together with GLP-1, GIP has an independent and additive effect on glucose dependent insulin secretion. Dual incretin compounds active at both the GLP-1 and GIP receptors have been shown to enhance endogenous insulin secretion in response to a glucose load, and demonstrate no apparent gastrointestinal effects compared to peptides active at the GLP-1 receptor alone.[14] GIP receptor agonists have been associated with modest weight loss in rodent models, and co-agonists have demonstrated enhanced weight loss in rodent and primate models in comparison to GLP-1 agonists alone.[15] There is also evidence that GIP activity may contribute to beta cell survival and function.[16] Finally, GIP has been demonstrated to enhance glucagon secretion in type 1 and type 2 diabetes patients in the setting of hypoglycemia, suggesting a potential therapeutic role in hypoglycemic protection for patients receiving insulin therapy.[17,18]

BRIEF SUMMARY OF THE INVENTION

In one aspect, the invention provides aqueous pharmaceutical formulations containing an incretin-insulin conjugate which are stable and which provide a protracted pharmacodynamics profile. Such formulations include L-arginine HCl and phenol (or m-cresol) as stabilizing agents. L-arginine HCl was also shown to modify the size distribution profile of the tri-agonist incretin-insulin conjugate's high-order structure leading to a more protracted pharmacodynamics profile when tested in mini-pig models. In one aspect, the aqueous pharmaceutical formulations are suitable for administration by injection.

In another aspect, the invention further provides an aqueous pharmaceutical formulation comprises (i) a therapeutically effective amount of an incretin-insulin conjugate which comprises an incretin peptide and an insulin molecule, (ii) a buffer (iii) glycerin, (iv) phenol or m-cresol, and (v) L-arginine HCl, wherein the pharmaceutical formulation has a pH of about 6.9 to about 7.5;

wherein the incretin peptide has the structure:
$X_1X_2X_3GX_4FTSDX_5SX_6YLDX_7X_8AAX_9X_{10}FVX_{11}WLLX_{12}X_{13}GPSSGAPPPSX_{14}$
wherein
$X_1$ is His, Tyr, or absent;
$X_2$ is aminoisobutyric acid;
$X_3$ is Glu or Gln; $X_4$ is Thr or Ile;
$X_5$ is Tyr or Lys acylated with a $C_{16}$ to $C_{20}$ alkyl group optionally via a gamma Glu linker;
$X_6$ is Ile or Arg;
$X_7$ is Lys, Arg, or Glu;
$X_8$ is Gln or Arg;
$X_9$ is Gln or aminoisobutyric acid;
$X_{10}$ is Glu or Asp;
$X_{11}$ is Asn, Gln, or Ala;
$X_{12}$ is Ala or Asp;
$X_{13}$ is Ala or Gly; and
$X_{14}$ is absent, or Lys, or acylated with a $C_{16}$ to $C_{20}$ alkyl group optionally via a gamma Glu; and
wherein the insulin molecule comprises an A chain polypeptide and a B chain polypeptide of human insulin, wherein the B chain is linked to said A chain through disulfide linkages and wherein the incretin peptide is linked to the insulin peptide via a linear chain spacer of 5 to 10 atoms, wherein the spacer comprises a disulfide linkage within the backbone of the spacer linear chain, said linear chain spacer joining the carboxy terminus of the incretin peptide to the side chain of an amino acid at position B1 of the B chain.

In a general embodiment of any of the above, the incretin peptide is
(i) $YX_2EGTFTSDYSIYLDKQAAX_9EFVNWLLAGGP-SSGAPPPS$, wherein $X_2$ and $X_9$ are each independently aminoisobutyric acid (SEQ ID NO:4)
(ii) $YX_2EGTFTSDX_5SIYLDKQAAX_9EFVNWLLAGG-PSSGAPPPS$, wherein $X_2$ and $X_9$ are each independently aminoisobutyric acid, and $X_5$ is Lys acylated with a $C_{16}$ fatty acyl group via gamma-Glu spacer (SEQ ID NO:5);
(iii) $YX_2EGTFTSDYSIYLDKQAAX_9EFVNWLLAGGP-SSGAPPPSX_{14}$, wherein $X_2$ and $X_9$ are each independently aminoisobutyric acid, and $X_{14}$ is Lys acylated with a $C_{16}$ fatty acyl group via gamma-Glu spacer (SEQ ID NO:6);
(iv) $HX_2EGTFTSDX_5SRYLDERAAQEFVAWLLDAGP-SGAPPPSK$, wherein $X_2$ is aminoisobutyric acid and $X_5$ is Lys acylated with a $C_{16}$ fatty acyl group via gamma-Glu spacer (SEQ ID NO:7);
(v) $HX_2QGTFTSDX_5SRYLDERAAQDFVQWLLDAG-PSGAPPPSK$, wherein $X_2$ is aminoisobutyric acid and $X_5$ is Lys acylated with a $C_{16}$ fatty acyl group via gamma-Glu spacer (SEQ ID NO:8);
(vi) $HX_2QGTFTSDX_5SRYLDERAAQDFVQWLLDGG-PSGAPPPSK$, wherein $X_2$ is aminoisobutyric acid and $X_5$ is Lys acylated with a $C_{16}$ fatty acyl group via gamma-Glu spacer (SEQ ID NO:9);
(vii) $HX_2EGTFTSDX_5SRYLDERAAQDFVQWLLDGG-PSGAPPPSK$, wherein $X_2$ is aminoisobutyric acid and $X_5$ is Lys acylated with a $C_{16}$ fatty acyl group via gamma-Glu spacer (SEQ ID NO:10); or
(viii) $X_2EGTFTSDX_5SIYLDKQAAX_9EFVNWLLAGGP-SGAPPPS$, wherein $X_2$ and $X_9$ are each independently aminoisobutyric acid and $X_5$ is Lys acylated with a $C_{16}$ fatty acyl group via gamma-Glu spacer (SEQ ID NO:11).

In one aspect of the invention, the incretin peptide is $YX_2EGTFTSDX_5SIYLDKQAAX_9EFVNWLLAGGPSS-GAPPPS$, wherein $X_2$ and $X_9$ are each independently aminoisobutyric acid, and $X_5$ is Lys acylated with a $C_{16}$ fatty acyl group via gamma-Glu (SEQ ID NO:5).

In any of the above embodiments, the linear chain spacer joining the incretin peptide to the insulin molecule comprises the general structure of:

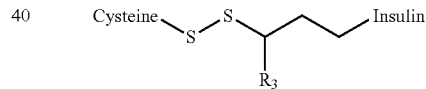

wherein $R_3$ is H or $CH_3$. In one embodiment, $R_3$ is H. In another embodiment, $R_3$ is $CH_3$.

In particular embodiments of any of the above described aqueous pharmaceutical formulations, said formulation comprises about 1 mg/mL to about 100 mg/mL, about 1 mg/mL to about 75 trig/mL, about 1 mg/mL to about 50 mg/mL, about 1 mg/mL to about 35 mg/mL or about 4 mg/mL to about 10 mg/mL of the incretin-insulin conjugate, about 5 mM to about 20 mM of the buffer, about 12 to about 20 mg/mL of glycerin, about 4 to about 6 mg/mL of phenol or m-cresol, about 5 to about 15 mg/mL of L-Arginine HCl, wherein the formulation has a pH of about 6.9 to about 7.5.

In some embodiments of the aqueous formulation comprises phenol. In other embodiments, the aqueous formulation comprises about 4 to about 6 mg/mL of phenol. In particular embodiments, the aqueous formulation comprises 5.0 mg/mL of phenol.

In some embodiments of any of the above, the aqueous pharmaceutical formulation of comprises a phosphate buffer. In another embodiment, the buffer is a tris buffer. In a further embodiment, the buffer is a histidine buffer. In another embodiment, the buffer is a phosphate buffer. In another embodiment, the phosphate buffer is sodium phosphate dibasic. In further embodiments, the formulation comprises about 10 mM of sodium phosphate dibasic.

In another embodiment, the aqueous pharmaceutical formulation comprises about 5 mg/mL to about 15 mg/mL of L-Arginine HCl. In particular embodiments, the aqueous pharmaceutical formulation comprises about 10.53 mg/mL of L-arginine HCl.

In some embodiments, the aqueous formulation comprises about 6.3 mg/mL, of the incretin-insulin conjugate, about 16 mg/mL of glycerin, about 5.0 mg/mL of phenol, about 10 mM sodium phosphate dibasic, about 10.53 mg/mL of L-Arginine HCl, wherein the pH of the formulation is about 7.2.

In any of the above embodiments, the incretin-insulin conjugate is selected from the group consisting of compound 99, compound 100, compound 101, compound 102, compound 103, compound 104, compound 105, or compound 106. In one embodiment, the incretin-insuling conjugate is compound 100.

In particular embodiments of any of the above described formulations, the aqueous pharmaceutical formulation does not contain zinc.

The aqueous pharmaceutical formulations described herein result in a protracted pharmacokinetic profile as compared to an aqueous pharmaceutical formulation which does not contain L-Arginine HCl.

In one aspect, the invention also provide a method of treating a patient or individual having a metabolic disease, comprising administering to the patient or individual an effective amount of any of the aqueous pharmaceutical formulations described herein to treat the metabolic disease in the patient or individual. In some embodiments, the metabolic disease is diabetes, non alcoholic fatty liver disease (NAFLD), non-alcoholic steatohepatitis (NASH), or obesity. In further embodiments, the diabetes is Type I diabetes, Type II diabetes, or gestational diabetes.

In another aspect, the invention also provides for use of any of the aqueous formulations described herein for the manufacture of a medicament for treatment of a metabolic disease. Also provided is use of any of the aqueous formulations described herein for treatment of a metabolic disease. In one embodiment, the metabolic disease is diabetes, non alcoholic fatty liver disease (NAFLD), non-alcoholic steatohepatitis (NASH), or obesity. In another embodiment, the diabetes is Type I diabetes, Type II diabetes, or gestational diabetes.

BRIEF DESCRIPTION OF THE DRAWINGS

FIG. 3a represents the impact of zinc, m-cresol and phenol on SEC-HMWS at 40° C. FIG. 3b represents the impact of various excipients on SEC-HMWS at 40° C. Zinc accelerates aggregation rate of compound 100 while phenol and arginine stabilize compound 100 against aggregation.

FIG. 4a represents the impact of zinc, m-cresol and phenol on RP-purity at 40° C. FIG. 4b represents impact of various excipients on RP-purity at 40° C. Zinc destabilized compound 100 and chemical degradation rate while phenol and arginine stabilizes the compound 100 and reduces chemical degradation rate.

FIG. 7a represents plasma glucose as a function of time. FIG. 7b represents the change of plasma glucose from baseline as a function of time.

FIG. 8a represents monomer, dimer and hexamer formation of RHI. FIG. 8b represents the micelle assembly of liraglutide. FIG. 8c represents alternate hypothetical multimerization models for compound 100 in the absence and presence of zinc ions

DETAILED DESCRIPTION OF THE INVENTION

I. Definitions and Abbreviations

Figure 1:
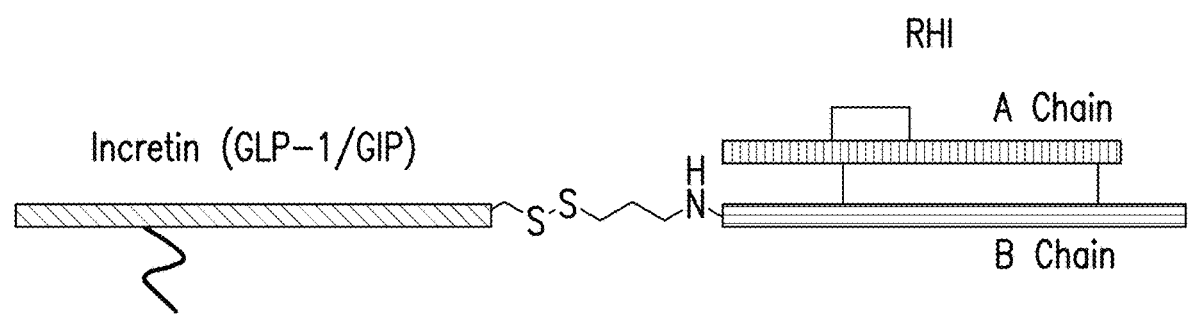
FIG. 1 is a schematic of compound 100, which is an incretin-insulin conjugate, wherein the incretin peptide is a GLP-1/GIP agonist connected to the B chain of recombinant human insulin via a linker.

As used throughout the specification and appended claims, the following abbreviations apply:
SV-AUC: sedimentation velocity-analytical ultra-centrifugation
DLS: Dynamic Light Scattering
PD: Pharmacodynamics
TI: Therapeutical index
T1DM: Type 1 diabetes mellitus
T2DM: Type 2 diabetes mellitus
RHI: Recombinant human insulin
GLP-1: Glucagon-like peptide-1
GIP: Gastric inhibitory polypeptide
QD: Quaque die
% per D: percent per day
SEC-HMWS: size exclusion chromatography-high molecular weight species
RP-purity: Reverse phase-purity
UPLC: Ultra performance liquid chromatography
SEC: Size exclusion chromatography
PDA: Photodiode array detector
ThT: Thioflavin T
FU: Fluorescence unit
rHSA: recombinant human serum albumin So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

Reference to "or" indicates either or both possibilities unless the context clearly dictates one of the indicated possibilities. In some cases, "and/or" was employed to highlight either or both possibilities.

As used herein, including the appended claims, the singular forms of words such as "a," "an," and "the," include their corresponding plural references unless the context clearly dictates otherwise.

The term "about", when modifying the quantity (e.g., mg/mL) of a substance or composition, the pH of a solution/formulation, or the value of a parameter characterizing a step in a method, or the like refers to variant in the numerical quantity that can occur, for example, through typical measuring, handling and sampling procedures involved in the preparation, characterization and/or use of the substance or composition; through inadvertent error in these procedures, through differences in the manufacture, source or purity of the ingredients employed to make or use the compositions or carryout the procedures and the like. In certain embodiments, "about" can mean a variation of greater or lesser than the value or range of values stated by 10 percent, e.g., ±0.2%, 0.5%, 1%, 2%, 3%, 4%, 5%, or 10%. Each value or range of values preceded by the term "about" is also intended to encompass the embodiment of the stated absolute value or range of values.

"Comprising" or variations such as "comprise", "comprises" or "comprised of" are used throughout the specification and claims in an inclusive sense, i.e., to specify the presence of the stated features but not to preclude the presence or addition of further features that may materially enhance the operation or utility of any of the embodiments of the invention, unless the context requires otherwise due to express language or necessary implication.

"Consists essentially of," and variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified composition or method. As a non-limiting example, an incretin-insulin conjugate that consists essentially of a recited amino acid sequence may also include one or more amino acids, including substitutions of one or more amino acid residues, which do not materially affect the properties of the binding compound.

The term "individual" is meant to include humans and companion or domesticated animals such as dogs, cats, horses, and the like. Therefore, the incretin-insulin conjugate formulations disclosed herein are also useful for treating or preventing obesity and obesity-related disorders in cats and dogs. As such, the term "mammal" includes humans and companion animals such as cats and dogs.

A "stable" formulation is one in which the protein therein essentially retains its physical stability and/or chemical stability and/or biological activity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10:29-90 (1993). Stability can be measured at a selected temperature for a selected time period.

As used herein, the term "treating" includes prophylaxis of the specific disorder or condition, or alleviation of the symptoms associated with a specific disorder or condition and/or preventing or eliminating said symptoms. For example, as used herein the term "treating diabetes" will refer in general to altering glucose blood levels in the direction of normal levels and may include increasing or decreasing blood glucose levels depending on a given situation.

As used herein an "effective" amount or a "therapeutically effective amount" means the total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. It refers to the amount of an incretin-insulin conjugate that is nontoxic but sufficient to provide the desired effect. For example one desired effect would be the prevention or treatment of hyperglycemia, e.g., as measured by a change in blood glucose level closer to normal, or treatment of obesity by inducing weight loss and/or preventing weight gain, e.g., as measured by reduction in body weight, or preventing or reducing an increase in body weight, or normalizing body fat distribution. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation. When applied to an individual active ingredient, administered alone, the term refers to that ingredient alone. When applied to a combination, the term refers to combined amounts of the active ingredients that result in the therapeutic effect, whether administered in combination, serially, or simultaneously.

The term, "parenteral" means not through the alimentary canal but by some other route, e.g., subcutaneous, intramuscular, intraspinal, or intravenous.

Figure 7A:
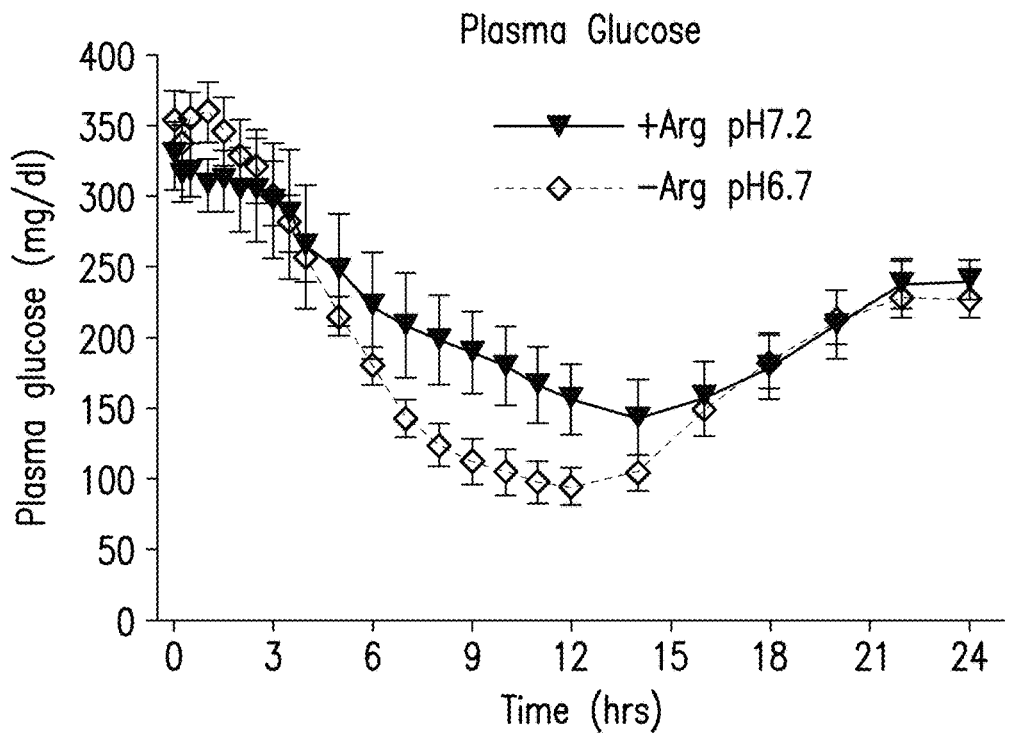
FIGS. 7a and 7b show pharmacodynamic profiles of two candidate formulations in mini pigs.
Figure 7B:
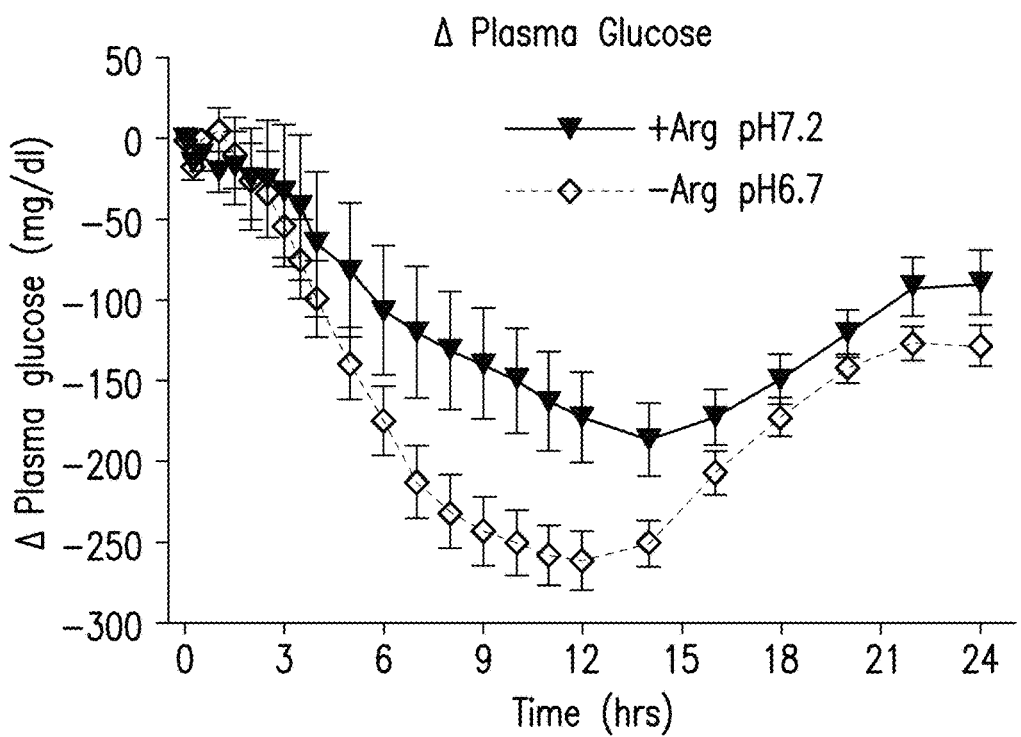

The term "peptide" as used herein encompasses a chain of 3 or more amino acids and typically less than 100 amino acids, wherein the amino acids are naturally occurring or coded or non-naturally occurring or non-coded amino acids. Non-naturally occurring amino acids refer to amino acids that do not naturally occur in vivo but which, nevertheless, can be incorporated into the peptide structures described herein. "Non-coded" as used herein refers to an amino acid that is not an L-isomer of any of the following 20 amino acids: Ala, Cys, Asp, Glu, Phe, Gly, His He, Lys, Leu, Met, Asn, Pro, Gln, Arg, Ser, Thr, Val, Trp, Tyr. "Coded" as used herein refers to an amino acid that is an L-isomer of any of the following 20 amino acids: Ala, Cys, Asp, Glu, Phe, Gly, His He, Lys, Leu, Met, Asn, Pro, Gln, Arg, Ser, Thr, Val, Trp, Tyr, As used herein, the term "protracted pharmacokinetic profile" is a pharmacokinetic profile which has a longer duration as compared to a reference pharmacokinetic profile. As a non-limiting example, as shown in FIGS. 7a and 7b, the formulations described herein containing arginine HCl when administered in the mini pig model exhibit a maximum effect on reducing plasma glucose 14 hours after administration, whereas a formulation not containing arginine HCl when similarly administered exhibits a maximum effect on reducing plasma glucose 12 hours after administration.

The term "Obesity" as used herein describes a condition in which there is an excess of body fat. The operational definition of obesity is based on the Body Mass Index (BMI), calculated as body weight per height in meters squared (kg/m2). "Obesity" refers to a condition whereby an otherwise healthy subject has a Body Mass Index (BMI) greater than or equal to 30 kg/m2, or a condition whereby a subject with at least one co-morbidity has a BMI greater than or equal to 27 kg/m2. An "obese subject" is an otherwise healthy subject with a Body Mass Index (BMI) greater than or equal to 30 kg/m2 or a subject with at least one co-morbidity with a BMI greater than or equal to 27 kg/m2. A "subject at risk for obesity" is an otherwise healthy subject with a BMI of 25 kg/m2 to less than 30 kg/m2 or a subject with at least one co-morbidity with a BMI of 25 kg/m2 to less than 27 kg/m2.

The increased risks associated with obesity occur at a lower Body Mass Index (BMI) in Asians. In Asian countries, including Japan, "obesity" refers to a condition whereby a subject with at least one obesity-induced or obesity-related co-morbidity that requires weight reduction or that would be improved by weight reduction, has a BMI greater than or equal to 25 kg/m2. In Asian countries, including Japan, an "obese subject" refers to a subject with at least one obesity-induced or obesity-related co-morbidity that requires weight reduction or that would be improved by weight reduction, with a BMI greater than or equal to 25 kg/m2. In Asian countries, a "subject at risk of obesity" is a subject with a BMI of greater than 23 kg/m2 to less than 25 kg/m2.

As used herein, the term "obesity" is meant to encompass all of the above definitions of obesity.

Obesity-induced or obesity-related co-morbidities include, but are not limited to, diabetes, non-insulin dependent diabetes mellitus—type 2, impaired glucose tolerance, impaired fasting glucose, insulin resistance syndrome, dyslipidemia, hypertension, hypentricacidemia, gout, coronary artery disease, myocardial infarction, angina pectoris, sleep apnea syndrome, Pickwickian syndrome, non-alcoholic fatty liver disease (NAFLD), non-alcoholic steatohepatitis (NASH), fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

Treatment of obesity and obesity-related disorders) refers to the administration of the compounds of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The formulations of the present invention are also useful for reducing the risk of secondary outcomes of obesity, such as reducing the risk of left ventricular hypertrophy.

The term "diabetes," as used herein, includes both insulin-dependent diabetes mellitus (IDDM, also known as type I diabetes) and non-insulin-dependent diabetes mellitus (NIDDM, also known as Type II diabetes). Type I diabetes, or insulin-dependent diabetes, is the result of an absolute deficiency of insulin, the hormone which regulates glucose utilization. Type II diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type II diabetics are also obese. The formulations of the present invention are useful for treating both Type I and Type II diabetes. The formulations are especially effective for treating Type II diabetes. The formulations of the present invention are also useful for treating and/or preventing gestational diabetes mellitus.

II. Incretin-Insulin Conjugates Useful in the Invention

As used herein, the term "incretin-insulin conjugate" describes a conjugate formed between an insulin molecule and an incretin, including for example a glucagon, GLP-I, or GIP agonist, a GLP-1/GIP co-agonist, a GLP-1/glucagon co-agonist or a glucagon/GLP-1/GIP tri-agonist, wherein the incretin-insulin conjugate has agonist activity at both the insulin receptor and the corresponding incretin receptor. Such conjugates are expected to have beneficial properties, including, for example, for treatment of diabetes while stimulating weight loss or preventing weight gain. Certain of the incretin-insulin conjugates disclosed herein are insulin/ glucagon-likepeptide-1 (GLP-1)/glucose-dependent insulinotropic polypeptide (GIP) tri-agonists which provide superior glycemic efficacy with an otherwise comparable profile to insulin/GLP-1 fixed dose combinations, or equal glycemic efficacy with a significantly lower risk of hypoglycemia. Examples on incretin-insulin conjugates which are useful in the formulations and methods, medicaments and uses of the present invention are include those described herein as well as those described in International Application Publication Nos. WO 2016/049190 A1 and WO 2014/158900 A.

The term "incretin" as used herein describes a group of gastrointestinal hormones that are involved in a wide variety of physiological functions, including glucose homeostasis, insulin secretion, gastric emptying, and intestinal growth, as well as the regulation of food intake. Pre-proglucagon is a 158 amino acid precursor polypeptide that is processed in different tissues to form a number of different peptides. Incretins include a number of proglucagon-derived peptides, including glucagon, glucagon-like peptide-1, glucagon-like peptide-2 and oxyntomodulin. Glucagon is a 29-amino acid peptide that corresponds to amino acids 33 through 61 of pre-proglucagon while GLP-1 is produced as a 37 amino acid peptide that corresponds to amino acids 72 through 108 of pre-proglucagon. GLP-1 (7-36) amide or GLP-1 (7-37) acid are biologically potent forms of GLP-1, that demonstrate essentially equivalent activity at the GLP-1 receptor. Incretins are described more fully in International Application Publication No. WO 2016/049190 A1, WO 2014/158900 A1, WO 2009/155258, WO 2009/058734, WO 2011/094337, WO 2009/148089, WO 2011/163473 and WO 2010/071807, the disclosures of each of which are expressly incorporated herein in their entirety.

The term "Insulin" or "Insulin molecule" as used herein refers to native insulin or any known insulin analog that has activity at the insulin receptor including, for example, any insulin molecule disclosed in published international applications W096/34882, WO 2010/080607, WO 2010/080609, WO 2011/159882, WO 2011/159895, and WO 2016/049190 and U.S. Pat. No. 6,630,348. Native insulin is biosynthesized as a larger linear precursor of low potency (approximately 2% to 9% of native insulin), named proinsulin. Proinsulin is proteolytically converted to insulin by the selective removal of a 35-residue connecting peptide (C peptide). The resultant heteroduplex formed by disulfide links between the insulin "A chain" (SEQ ID NO: 2) and "B chain" (SEQ ID NO: 3) chain, representing a total of 51 amino acids, has high potency for the insulin receptor (nM range). Native insulin has approximately one hundredfold selective affinity for the insulin receptor relative to the related insulin-like growth factor 1 receptor, but demonstrates little selectively for the two different insulin receptor isoforms, named A & B.

III. Formulations of the Invention

In one aspect, the invention provides aqueous pharmaceutical formulations comprising (i) a therapeutically effective amount of an incretin-insulin conjugate which comprises an incretin peptide and an insulin molecule, (ii) a buffer (iii) glycerin, (iv) phenol or m-cresol, and (v) L-arginine HCl, wherein the pharmaceutical formulation has a pH of about 6.9 to about 7.5.

In one embodiment, the incretin peptide of the incretin-insulin conjugate has the structure:

(SEQ ID NO: 1)
$X_1X_2X_3GX_4FTSDX_5SX_6YLDX_7X_8AAX_9X_{10}FVX_{11}WLLX_{12}X_{13}GPSSGAPP$
$PSX_{14}$ wherein
$X_1$ is His, Tyr, or absent;
$X_2$ is atninoisobuttyic acid;
$X_3$ is Glu or Gln;
$X_4$ is Thr or Ile;
$X_5$ is Tyr or Lys acylated with a $C_{16}$ to $C_{20}$ alkyl group optionally via a gamma Glu linker;
$X_6$ is Ile or Arg;
$X_7$ is Lys, Arg, or Glu;
$X_8$ is Gln or Arg;
$X_9$ is Gln or aminoisobutyric acid;
$X_{10}$ is Glu or Asp;
$X_{11}$ is Asn, Gln, or Ala;
$X_{12}$ is Ala or Asp;
$X_{13}$ is Ala or Gly; and
$X_{14}$ is absent, or Lys, or Lys acylated with a $C_{16}$ to $C_{20}$ alkyl group optionally via a gamma Glu; and
the insulin molecule of the incretin-insulin conjugate comprises an A chain polypeptide and a B chain polypeptide of human insulin, wherein the B chain is linked to said A chain through disulfide linkages and wherein the incretin peptide is linked to the insulin peptide via a linear chain spacer of 5 to 10 atoms, wherein the spacer comprises a disulfide linkage within the backbone of the spacer linear chain, said linear chain spacer joining the carboxy terminus of the incretin peptide to the side chain of an amino acid at position B1 of the B chain. A schematic of such an incretin-insulin conjugate is exemplified in FIG. 1.

In another embodiment, the incretin peptide of the incretin-insulin conjugate is selected from any one of the following:

(i) $YX_2EGTFTSDYSIYLDKQAAX_9$ EFVNWL-LAGGPSSGAPPPS, wherein $X_2$ and $X_9$ are each independently aminoisobutyric acid, (SEQ ID NO: 4);

(ii) $YX_2EGTFTSDX_5SIYLDKQAAX_9EFVNWLLAGG$-PSSGAPPPS, wherein $X_2$ and $X_9$ are each independently aminoisobutyric acid, and $X_5$ is Lys acylated with a $C_{16}$ fatty acyl group via gamma-Glu spacer (SEQ ID NO: 5);

(iii) $YX_2EGTFTSDYSIYLDKQAAX_9EFVNWLLAGG$P-SSGAPPPSX$_{14}$, wherein $X_2$ and $X_9$ are each independently aminoisobutyric acid, and $X_{14}$ is Lys acylated with a $C_{16}$ fatty acyl group via gamma-Glu spacer (SEQ ID NO: 6);

(iv) $HX_2EGTFTSDX_5SRYLDERAAQEFVAWLLDAGP$-SGAPPPSK, wherein $X_2$ is aminoisobutyric acid and $X_5$ is Lys acylated with a $C_{16}$ fatty acyl group via gamma-Glu spacer (SEQ ID NO: 7);

(v) $HX_2QGTFTSDX_5SRYLDERAAQDFVQWLLDAG$-PSGAPPPSK, wherein $X_2$ is aminoisobutyric acid and $X_5$ is Lys acylated with a $C_{16}$ fatty acyl group via gamma-Glu spacer (SEQ ID NO: 8);

(vi) $HX_2QGTFTSDX_5SRYLDERAAQDFVQWLLDGG$-PSGAPPPSK, wherein $X_2$ is aminoisobutyric acid and $X_5$ is Lys acylated with a $C_{16}$ fatty acyl group via gamma-Glu spacer (SEQ ID NO: 9);

(vii) HX$_2$EGTFTSDX$_5$SRYLDERAAQDFVQWLLDGG-PSGAPPPSK, wherein $X_2$ is aminoisobutyric acid and $X_5$ is Lys acylated with a $C_{16}$ fatty acyl group via gamma-Glu spacer (SEQ ID NO: 10); and (viii) X$_2$EGTFTSDX$_5$SIYLDKQAAX$_9$EFVNWLLAGGP-SGAPPPS, wherein $X_2$ and $X_9$ are each independently aminoisobutyric acid and $X_5$ is Lys acylated with a $C_{16}$ fatty acyl group via gamma-Glu spacer (SEQ ID NO: 11).

In another embodiment, the incretin peptide is YX$_2$EGTFTSDX$_5$SIYLDKQAAX$_9$EFVNWLLAGGPSS-GAPPPS, wherein $X_2$ and $X_9$ are each independently aminoisobutyric acid, and $X_5$ is Lys acylated with a $C_{16}$ fatty acyl group via gamma-Glu (SEQ ID NO: 5)

In some embodiments, the linear chain spacer joining the incretin peptide to the insulin molecule comprises the general structure of:

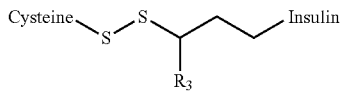

wherein $R_3$ is H or $CH_3$. Additional linear chain spacers joining the incretin peptide to the insulin molecule may include any such spacers known in the art, including those described in International Application Publication No. WO 2016/049190 A1.

In some embodiments, the cysteine of the linear chain spacer joining the incretin peptide to the insulin molecule is at the C-terminal end of the incretin peptide, as exemplified below in each of SEQ ID NOs: 12-19.

(i) YX$_2$EGTFTSDYSIYLDKQAAX$_9$EFVNWLLAGGP-SSGAPPPSC, wherein $X_2$ and $X_9$ are each independently aminoisobutyric acid (SEQ ID NO:12)

(ii) YX$_2$EGTFTSDX$_5$SIYLDKQAAX$_9$EFVNWLLAGG-PSSGAPPPSC, wherein $X_2$ and $X_9$ are each independently aminoisobutyric acid, and $X_5$ is Lys acylated with a $C_{16}$ fatty acyl group via gamma-Glu spacer (SEQ ID NO:13);

(iii) YX$_2$EGTFTSDYSIYLDKQAAX$_9$EFVNWLLAGGP-SSGAPPPSX$_{14}$C, wherein $X_2$ and $X_9$ are each independently aminoisobutyric acid, and $X_{14}$ is Lys acylated with a $C_{16}$ fatty acyl group via gamma-Glu spacer (SEQ ID NO:14);

(iv) HX$_2$EGTFTSDX$_5$SRYLDERAAQEFVAWLLDAGP-SGAPPPSKC, wherein $X_2$ is aminoisobutyric acid and $X_5$ is Lys acylated with a $C_{16}$ fatty acyl group via gamma-Glu spacer (SEQ ID NO:15);

(v) HX$_2$QGTFTSDX$_5$SRYLDERAAQDFVQWLLDAG-PSGAPPPSKC, wherein $X_2$ is aminoisobutyric acid and $X_5$ is Lys acylated with a $C_{16}$ fatty acyl group via gamma-Glu spacer (SEQ ID NO:16);

(vi) HX$_2$QGTFTSDX$_5$SRYLDERAAQDFVQWLLDGG-PSGAPPPSKC, wherein $X_2$ is aminoisobutyric acid and $X_5$ is Lys acylated with a $C_{16}$ fatty acyl group via gamma-Glu spacer (SEQ ID NO:17);

(vii) HX$_2$EGTFTSDX$_5$SRYLDERAAQDFVQWLLDGG-PSGAPPPSKC, wherein $X_2$ is aminoisobutyric acid and $X_5$ is Lys acylated with a $C_{16}$ fatty acyl group via gamma-Glu spacer (SEQ ID NO:18); and (viii) X$_2$EGTFTSDX$_5$SIYLDKQAAX$_9$EFVNWLLAGGP-SGAPPPSC, wherein $X_2$ and $X_9$ are each independently aminoisobutyric acid and $X_5$ is Lys acylated with a $C_{16}$ fatty acyl group via gamma-Glu spacer (SEQ NO:19), In one embodiment, the S group of the Cys residue of the incretin of any one of SEQ ID NO: 12-19 is conjugated to the alpha amino group of the N-terminal Phe residue of the B-chain polypeptide of an insulin heterodimer having an A-chain polypeptide of SEQ ID NO: 2 and a B-chain polypeptide of SEQ ID NO: 3 via a linker having the structure S-CH2-CH2-CH2 in a disulfide linkage. In another embodiment, the incretin-insulin conjugate is YX$_2$EGTFTSDX$_5$SIYLDKQAAX$_9$EFVNWLLAGGPSS-GAPPPSC, wherein $X_2$ and $X_9$ are each independently aminoisobutyric acid, and $X_5$ is Lys acylated with a $C_{16}$ fatty acyl group via gamma-Glu spacer (SEQ ID NO:13) and wherein the S group of the Cys residue of the incretin of any one of SEQ ID NO: 12-19 is conjugated to the alpha amino group of the N-terminal Phe residue of the B-chain polypeptide of an insulin heterodimer having an A-chain polypeptide of SEQ ID NO: 2 and a B-chain polypeptide of SEQ ID NO: 3 via a linker having the structure S—CH2-CH2-CH2 in a disulfide linkage.

In another embodiment, the incretin-insulin conjugate is compound 99, 100, 101, 102, 103, 104, 105, or 106, as described in the table below.

| Compound | Description |
|---|---|
| Compound 99 | YX$_2$EGTFTSDYSIYLDKQAAX$_9$EFVNWLLAGGPSSGAPPPSC (SEQ ID NO: 12), wherein $X_2$ and $X_9$ are each independently aminoisobutyric acid and wherein the S group of the Cys residue of the incretin is conjugated to the alpha amino group of the N-terminal Phe residue of the B-chain polypeptide of an insulin heterodimer having an A chain polypeptide of SEQ ID NO: 2 and a B-chain polypeptide of SEQ ID NO: 3 via a linker having the structure S-CH$_2$-CH$_2$-CH$_2$ in a disulfide linkage. |
| Compound 100 | YX$_2$EGTFTSDX$_5$SIYLDKQAAX$_9$EFVNWLLAGGPSSGAPPPSC (SEQ ID NO: 13), wherein $X_2$ and $X_9$ are each independently aminoisobutyric acid, and $X_5$ is Lys acylated with a $C_{16}$ fatty acyl group via gamma-Glu spacer and wherein the S group of the Cys residue of the incretin is conjugated to the alpha amino group of the N-terminal Phe residue of the B-chain polypeptide of an insulin heterodimer having an A chain polypeptide of SEQ ID NO: 2 and a B-chain polypeptide of SEQ ID NO: 3 via a linker having the structure S-CH$_2$-CH$_2$-CH$_2$ in a disulfide linkage. |

| Compound | Description |
|---|---|
| Compound 101 | YX$_2$EGTFTSDYSIYLDKQAAX$_9$EFVNWLLAGGPSSGAPPPSX$_{14}$C (SEQ ID NO: 14), wherein X$_2$ and X$_9$ are each independently aminoisobutyric acid, and X$_{14}$ is Lys acylated with a C$_{16}$ fatty acyl group via gamma-Glu spacer and wherein the S group of the Cys residue of the incretin is conjugated to the alpha amino group of the N-terminal Phe residue of the B-chain polypeptide of an insulin heterodimer having an A chain polypeptide of SEQ ID NO: 2 and a B-chain polypeptide of SEQ ID NO: 3 via a linker having the structure S-CH$_2$-CH$_2$-CH$_2$ in a disulfide linkage. |
| Compound 102 | HX$_2$EGTFTSDX$_5$SRYLDERAAQEFVAWLLDAGPSGAPPPSKC (SEQ ID NO: 15), wherein X$_2$ is aminoisobutyric acid and X$_5$ is Lys acylated with a C$_{16}$ fatty acyl group via gamma-Glu spacer and wherein the S group of the Cys residue of the incretin is conjugated to the alpha amino group of the N-terminal Phe residue of the B-chain polypeptide of an insulin heterodimer having an A chain polypeptide of SEQ ID NO: 2 and a B-chain polypeptide of SEQ ID NO: 3 via a linker having the structure S-CH$_2$-CH$_2$-CH$_2$ in a disulfide linkage. |
| Compound 103 | HX$_2$QGTFTSDX$_5$SRYLDERAAQDFVQWLLDAGPSGAPPPSKC (SEQ ID NO: 16), wherein X$_2$ is aminoisobutyric acid and X$_5$ is Lys acylated with a C$_{16}$ fatty acyl group via gamma-Glu spacer and wherein the S group of the Cys residue of the incretin is conjugated to the alpha amino group of the N-terminal Phe residue of the B-chain polypeptide of an insulin heterodimer having an A chain polypeptide of SEQ ID NO: 2 and a B-chain polypeptide of SEQ ID NO: 3 via a linker having the structure S-CH$_2$-CH$_2$-CH$_2$ in a disulfide linkage. |
| Compound 104 | HX$_2$QGTFTSDX$_5$SRYLDERAAQDFVOWLLDGGPSGAPPPSKC (SEQ ID NO: 17), wherein X$_2$ is aminoisobutyric acid and X$_5$ is Lys acylated with a C$_{16}$ fatty acyl group via gamma-Glu spacer and wherein the S group of the Cys residue of the incretin is conjugated to the alpha amino group of the N-terminal Phe residue of the B-chain polypeptide of an insulin heterodimer having an A chain polypeptide of SEQ ID NO: 2 and a B-chain polypeptide of SEQ ID NO: 3 via a linker having the structure S-CH$_2$-CH$_2$-CH$_2$ in a disulfide linkage. |
| Compound 105 | HX$_2$EGTFTSDX$_5$SRYLDERAAQDFVQWLLDGGPSGAPPPSKC (SEQ ID NO: 18), wherein X$_2$ is aminoisobutyric acid and X$_5$ is Lys acylated with a C$_{16}$ fatty acyl group via gamma-Glu spacer and wherein the S group of the Cys residue of the incretin is conjugated to the alpha amino group of the N-terminal Phe residue of the B-chain polypeptide of an insulin heterodimer having an A chain polypeptide of SEQ ID NO: 2 and a B-chain polypeptide of SEQ ID NO: 3 via a linker having the structure S-CH$_2$-CH$_2$-CH$_2$ in a disulfide linkage. |
| Compound 106 | X$_2$EGTFTSDX$_5$SIYLDKQAAX$_9$EFVNWLLAGGPSGAPPPSC (SEQ ID NO: 19), wherein X$_2$ and X$_9$ are each independently aminoisobutyric acid and X$_5$ is Lys acylated with a C$_{16}$ fatty acyl group via gamma-Glu spacer and wherein the S group of the Cys residue of the incretin is conjugated to the alpha amino group of the N-terminal Phe residue of the B-chain polypeptide of an insulin heterodimer having an A chain polypeptide of SEQ ID NO: 2 and a B-chain polypeptide of SEQ ID NO: 3 via a linker having the structure S-CH$_2$-CH$_2$-CH$_2$ in a disulfide linkage. |
| Incretin portion of formula I conjugated to insulin | X$_1$X$_2$X$_3$GX$_4$FTSDX$_5$SX$_6$YLDX$_7$X$_8$AA$_9$X$_{10}$FVX$_{11}$WLLX$_{12}$X$_{13}$GPSSGAPPPSX$_{14}$C (SEQ ID NO: 20) wherein<br>X$_1$ is is, tyr, or absent;<br>X$_2$ is aminoisobutyric acid;<br>X$_3$ is Glu or Gln;<br>X$_4$ is Thr or Ile;<br>X$_5$ is Tyr or Lys acylated with a C$_{16}$ to C$_{20}$ alkyl group optionally via a gamma Glu linker;<br>X$_6$ is Ile or Arg;<br>X$_7$ is Lys, Arg, or Glu;<br>X$_8$ is Gln or Arg;<br>X$_9$ is Gln or aminoisobutyric acid;<br>X$_{10}$ is Glu or Asp;<br>X$_{11}$ is Asn, Gln, or Ala;<br>X$_{12}$ is Ala or Asp;<br>X$_{13}$ is Ala or Gly; and<br>X$_{14}$ is absent, or Lys, or Lys acylated with a C$_{16}$ to C$_{70}$ alkyl group optionally via a gamma Glu;<br>and wherein the S group of the Cys residue of the incretin is conjugated |

| Compound | Description |
|---|---|
| | to the alpha amino group of the N-terminal Phe residue of the B-chain polypeptide of an insulin heterodimer having an A chain polypeptide of SEQ ID NO: 2 and a B-chain polypeptide of SEQ ID NO: 3 via a linker having the structure S-CH$_2$-CH$_2$-CH$_2$ in a disulfide linkage. |

In another embodiment, the incretin-insulin conjugate is compound 100, a schematic of which is set forth in FIG. 1.

In a particular embodiment of the aqueous pharmaceutical formulation, the formulation comprises about 1 mg/mL, to about 100 mg/mL; about 1 mg/mL to about 50 mg/mL, about 50 mg/mL to about 100 mg/mL, about 1 mg/mL to about 25 mg/mL, about 50 mg/mL to about 75 mg/mL, about 25 mg/mL to about 75 mg/mL, about 1 mg/mL to about 10 mg/mL, or about 4 mg/mL to about 10 mg/mL of any of the incretin-insulin conjugates described herein or in International Application Publication No. WO 2016/049190. In a further embodiment, the aqueous pharmaceutical formulation comprises about 4, 5, 5.5, 6.0, 6.5, 7, 8, 9 or 10 mg/mL of the incretin-insulin conjugate. In another embodiment, the aqueous pharmaceutical formulation comprises about 5.7, 5.8, 5.9, 6.0, 6.1, 6.2, 6,3, 6.4, 6.5, 6.6, 6.7, 6.8, 6.9 or 7.0 mg/mL of the incretin-insulin conjugate. In another embodiment, the aqueous pharmaceutical formulation comprises about 6.3 mg/mL of the incretin-insulin conjugate.

In one embodiment, the aqueous pharmaceutical formulation comprises phenol or m-cresol. In one embodiment the aqueous pharmaceutical formulation contains m-cresol. In another embodiment the aqueous pharmaceutical formulation comprises phenol. The m-cresol or phenol may be present in the formulation in amounts ranging from about 1 mg/mL to about 20 mg/mL, about 1 mg/mL to about 10 mg/mL to about 4 mg/mL to about 6 mg/mL, or about 1 mg/mL to about 5 mg/mL. In a further embodiment, the phenol or m-cresol is present in an amount of about 5 mg/mL.

In one embodiment, the aqueous pharmaceutical formulation comprises a buffer, including, for example, a phosphate buffer, a tris buffer or a histidine buffer. In one embodiment, the buffer is a phosphate buffer. In a further embodiment, the phosphate buffer is phosphate buffer is sodium phosphate dibasic. In a further embodiment, the formulation comprises about 5 mM to about 20 mM of buffer. In another embodiment, the formulation comprises about 5 to about 15 mM buffer. In one embodiment, the formulation comprises about 10 mM of a phosphate buffer. In one embodiment, the formulation comprises about 10 mM of a tris buffer. In another embodiment, the formulation comprises about 10 mM of a histidine buffer. In a particular embodiment, the formulation comprises about 10 mM of sodium phosphate dibasic.

In on aspect of the aqueous pharmaceutical formulation, the formulation comprises from about 1 mg/mL, to about 20 mg/mL, about 5 mg/mL to about 20 mg/mL, about 10 mg/mL to about 20 mg/mL or about 12 mg/mL to about 20 mg/mL of glycerin. In particular embodiments, the formulation comprises about 12, 13, 14, 15, 16, 17, 18, 19, or 20 mg/mL of glycerin. In one embodiment, the aqueous pharmaceutical formulation comprises about 16 mg/mL of glycerin.

In one embodiment of the aqueous pharmaceutical formulation, the formulation comprises from about 5 mg/mL to about 15 mg/mL of L-arginine or a pharmaceutically acceptable salt thereof. In one embodiment, the formulation comprises about 5 mg/mL to about 15 mg/mL of L-arginine hydrochloride (L-Arginine HCl). In another embodiment, the formulation comprises about 10,48, 10.49, 10.5, 10.51, 10.52, 10.53, 10.54, 10.55, 10.56, 10.57, 10.58 L-arginine HCl. In a further embodiment, the aqueous pharmaceutical formulation comprises about 10.53 mg/mL of L-arginine HCl.

In particular embodiments of the aqueous pharmaceutical formulation, the formulation has a pH of from about 6.0 to about 8.0. In other embodiments, the pH of the formulation is from about 6.5 to about 7.5. In another embodiment, the is from about 6.9 to about 7.5. In some embodiments, the pH of the formulation is about 6.5, 6.6, 6.7, 6.8, 6.9, 7.0, 7.1, 7.2, 7.3, 7.4, or 7.5. In another embodiment, the pH of the formulation is about 7.2.

In particular embodiments, the aqueous pharmaceutical formulation comprises about 1 mg/mL to about 100 mg/mL, about 1 mg/mL to about 75 mg/mL, about 1 to about 50 mg/mL, about 1 mg/mL to about 35 mg/mL or about 4 mg/mL to about 10 mg/mL of any of the incretin-insulin conjugates described herein, about 5 mM to about 20 mM buffer, about 12 mg/mL to about 20 mg/mL of glycerin, about 4 mg/mL to about 6 mg/mL of phenol or m-cresol, about 5 mg/mL to about 15 mg/mL of L-Arginine HCl and the formulation has a pH of about 6.9 to about 7,5. In one embodiment, the buffer is a phosphate, tris or histidine buffer. In another embodiment, the buffer is a phosphate buffer. In a further embodiment, the phosphate buffer is sodium phosphate dibasic.

In another embodiment, the aqueous pharmaceutical formulation comprises about 6.3 mg/mL of the incretin-insulin conjugate, about 16 mg/mL of glycerin, about 5.0 mg/mL of phenol, about 10 mM sodium phosphate dibasic, about 10.53 mg/mL of L-Arginine HCl, wherein the pH of the formulation is about 7.2.

In another embodiment, the aqueous pharmaceutical formulation as described in any of the above embodiments does not contain zinc.

In one embodiment, administration of any of the aqueous pharmaceutical formulations described herein results in a protracted pharmacokinetic profile as compared to the same aqueous pharmaceutical formulation which does not contain L-Arginine HCl.

III. Methods of Treatment with and Use of the Formulations

The liquid pharmaceutical formulations are useful for the treatment of a metabolic disorder in an individual. Such disorders include, but are not limited to, obesity, metabolic syndrome or syndrome X, type II diabetes, complications of diabetes such as retinopathy, hypertension, dyslipidemias, cardiovascular disease, gallstones, osteoarthritis, and certain forms of cancers. The obesity-related disorders herein are associated with, caused by, or result from obesity. Thus, in one embodiment of the invention is a method of treating a patient or an individual having a metabolic disease, comprising administering to the patient an effective amount of any of the formulations described herein so as to treat the metabolic disease in the patient or individual.

In one embodiment, the metabolic disease is diabetes, non alcoholic fatty liver disease (NAFLD), non-alcoholic steatohepatitis (NASH), or obesity. In another embodiment, the diabetes is Type I diabetes, Type II diabetes, or gestational diabetes.

Also provided herein is use of any of the incretin-insulin conjugate formulations described herein for the manufacture of a medicament for treatment of a metabolic disease. Further provided is use of any of the incretin-insulin conjugate formulations described herein for the treatment of a metabolic disease. In some embodiments, the metabolic disease is diabetes, non alcoholic fatty liver disease (NAFLD), non-alcoholic steatohepatitis (NASH), or obesity. In further embodiments, the diabetes is Type I diabetes, Type II diabetes, or gestational diabetes.

Suitable routes of administration may, for example, include parenteral delivery, including intramuscular, subcutaneous, as well as intrathecal, direct intraventricular, intravenous, intraperitoneal. Drugs can be administered in a variety of conventional ways, such as intraperitoneal, parenteral, intraarterial or intravenous injection.

Selecting a dosage of the incretin-insulin conjugate depends on several factors, including the serum or tissue turnover rate of the entity, the level of symptoms, the immunogenicity of the entity, and the accessibility of the target cells, tissue or organ in the individual being treated. The dosage of the additional therapeutic agent should be an amount that provides an acceptable level of side effects. Accordingly, the dose amount and dosing frequency of the incretin-insulin conjugate will depend in part on the patient characteristics. Determination of the appropriate dosage regimen may be made by the clinician, e.g., using parameters or factors known or suspected in the art to affect treatment or predicted to affect treatment, and will depend, for example, the patient's clinical history (e.g., previous therapy), the type and stage of the cancer to be treated and biomarkers of response to one or more of the therapeutic agents in the combination therapy.

Further provided is a pharmaceutical pack or kit, comprising one or more containers filled with one or more of the liquid pharmaceutical formulations disclosed herein. Optionally associated with such container(s) may be a notice in the form prescribed by a governmental agency regulating the manufacture, use or sale of pharmaceuticals or biological products, which notice reflects approval by the agency of manufacture, use or sale for human administration.

The following examples are intended to promote a further understanding of the present invention.

Example 1

Preparation of Compound 100, an Incretin-Insulin Conjugate

Compound 100 was supplied as lyophilized powder. The powder was first reconstituted in water to a concentration of ~20 mg/mL. Formulations were prepared by spiking reconstituted Compound 100 with stock solutions of excipients. The pH of the formulation was adjusted to the desired value by either 1N HCl or NaOH. The final formulations were filtered through a 0.22 μm fitter (Steriflip®). Formulations were then filled into clean 2 mL vials in a laminar-flow hood. Filled vials were staged in the stability chamber for the following conditions: 5° C./ambient RH, 25° C./60% RH, and 40° C./75% RH.

Compound 100 and the other incretin-insulin conjugates disclosed herein are insulin-GLP1-GIP tri-agonists. Compound 100 was prepared by chemical conjugation of RHI at the B1 position with a lipidized incretin molecule composed of GLP-1 and GIP. Due to the intrinsic complexity of this molecule, an excipient screening study was conducted to study a panel of excipients and/or excipient combinations in order to identify (1) a formulation to best stabilize the molecule against physical and chemical degradation, and (2) a formulation to achieve a basal pharmacodynamic profile, i.e. 24-hr coverage with one SubQ injection. Table 3 lists the composition of each formulation (F0-F15) in this screening study. Phenol (in F14) and m-cresol (in F2-F13 and F15) were studied as preservatives since a multidose formulation is intended. Zinc was studied at three different levels (0, 0.3 mM, 0.6 mM) in F2, F3 and F13, respectively, in order to understand its impact on insulin hexamer formation. Glycerin was used as a tonicity modifier in most formulations; however, PEG400 and propylene glycol were used as both tonicity modifier and wetting agent in F11, F15 and F12 respectively. Glycerin was sourced from two manufacturers, either JT Baker (most formulations) or Hedinger (F10), allowing some evaluation with respect to Compound 100 stability. Other excipients studied include arginine (F4), recombinant human serum albumin (rHSA, F5), trehalose (F6), methionine (F7), Tris (F8), and an excipient combination (F9). All tested formulations were pH adjusted to 7.0 and followed on a short-term stability study up to 8 weeks at 40° C.

Example 2

Hydrodymanic Size Distribution Measurement of Compound 100 in Formulations F0-F15

Figure 2:
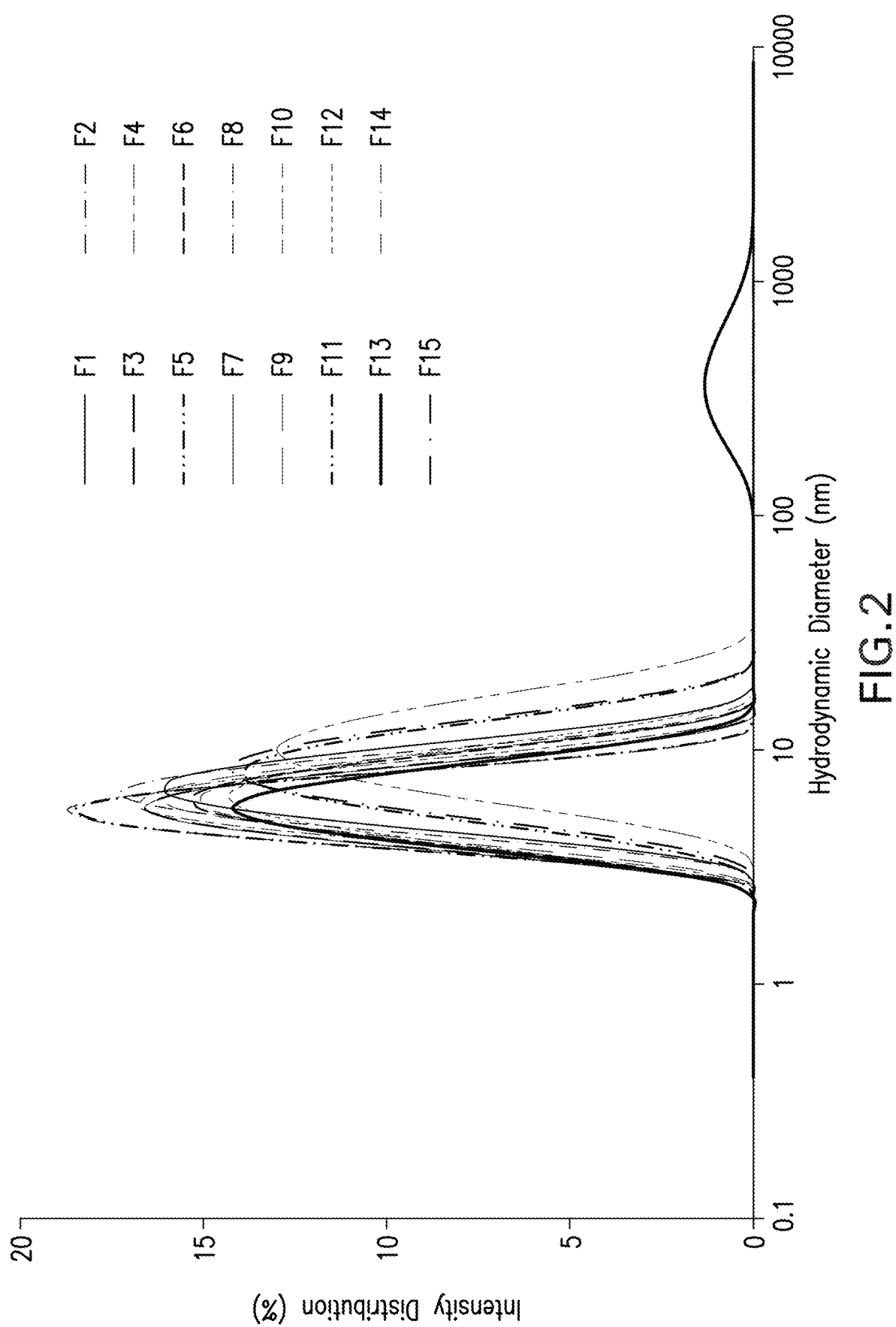
FIG. 2 shows the hydrodynamic size distribution of Compound 100 in different formulations. High zinc concentration leads to multi-modal distribution of Compound 100.

The hydrodynamic size distribution of Compound 100 in formulations F0-F15 was measured by Dynamic Light Scattering (DLS), the results of which are set forth in FIG. 2. Dynamic Light Scattering (DLS) was performed using a Zetasizer Nano ZS (Malvern Instruments, Worcestershire, UK) at an angle of 173° by utilizing a noninvasive backscatter technique. Measurements were conducted at 20° C. at ~6 mg/mL.

In most formulations, Compound 100 showed a mono-distribution with a Z-average diameter between 5-10 nm. Two peaks were, however, observed in F13 with the first peak around 6 nm and the second peak around 400 nm. The presence of the second peak (400 nm) in F13 is most likely due to the higher zinc concentration (0.6 mM) in this formulation which led to sub-visible particle formation. Visible precipitation was indeed observed in F13 after storage at 5° C. for a few weeks. This highlights the importance of tight zinc control in triagonist formulation. Excessive zinc in the formulation not only increases the risk of protein precipitation but also zinc phosphate precipitation once the solubility limit is exceeded.

Example 3

Compound 100 Stability by RP-UPLC and HP-SEC

Samples were run on a Waters Acquity UPLC with a PDA detector (214 nm). Gradient elution was performed using mixtures of Mobile Phase A as 0.2 M NaClO4, 0.05% HClO4 and Mobile Phase B as acetonitrile. 3.0 μg of sample was injected and run through a Waters BEH C8 1.7 μm, 2.1×150 mm column, with the column temperature at 40° C. Purity measurements were performed at 214 nm. The area of the main peak (purity) declined in a linear manner under accelerated/stressed condition. Chemical stability of the drug was expressed as the rate of decline in % per day.

Samples were run undiluted on a Waters Alliance 2695 with a Waters 2486 Dual Wavelength detector. A Mobile Phase of 1 mg/mL L-Arginine/acetonitrile/Glacial acetic acid (65:20:15) is flowed at a rate of 0.5 mL/rain. 30 µL of sample was injected and run through a Waters Insulin HMWP 7.8×300 mm, 3.5 µm column at room temperature. Detector wavelength was 276 nm. Analysis was performed using Empower 2, with data reported as a peak percentage of the total area. The area of the HMWS (high molecule weight species) increased in a linear manner under accelerated/stressed condition. Aggregation kinetics was expressed as the rate of increase in % per day.

Figure 3A:
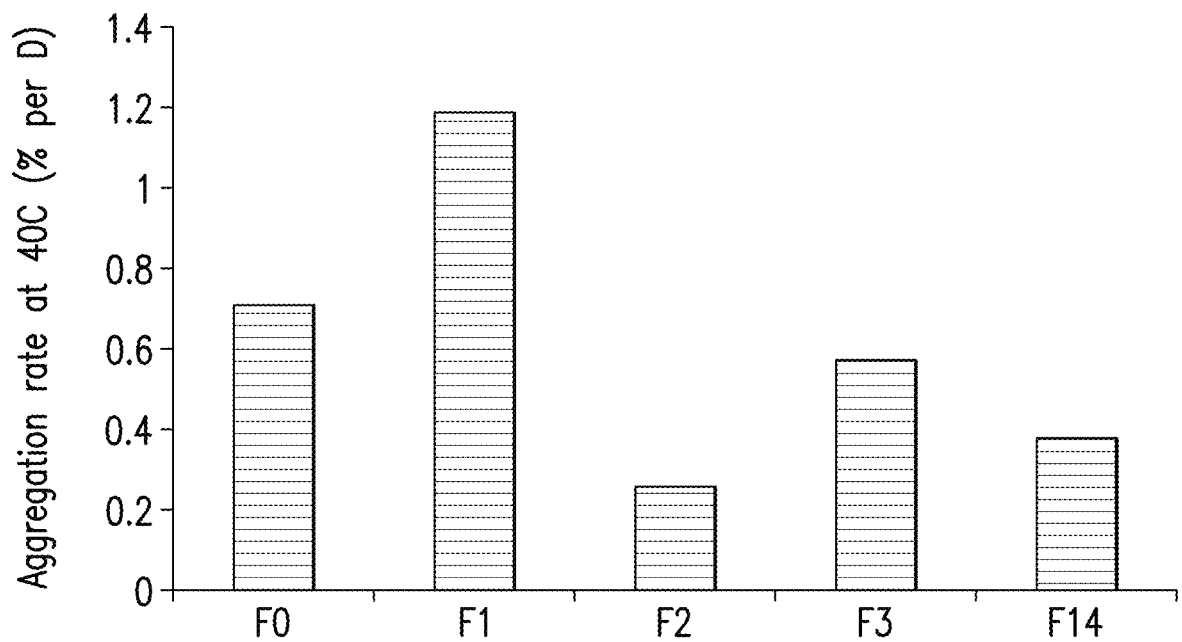
FIGS. 3a and 3b shows compound 100 stability as monitored by HP-SEC.

Aggregation is one of the major degradation pathways for Compound 100 which was followed in this short-term stability study. As shown in FIG. 3a, Compound 100 is the least stable in formulations containing zinc but not containing m-cresol (see, e.g., formulation F1). This is unexpected as most commercial insulin molecules are stabilized by the formation of hexamers with the addition of zinc in their drug product formulations. This suggests that zinc does not trigger the formation of classical insulin hexamer in Compound 100 formulations (discussed later in Example 8). Compared to formulation F1, formulation F2 (zinc free, m-cresol containing) displayed significantly better stability against aggregate formation. Interestingly, the stability of formulation F3 (zinc containing, m-cresol containing) is superior to F1 but inferior to F2. Taking all this into consideration, m-cresol is likely a stabilizer but zinc is likely a destabilizer for Compound 100 and the other incretin-insulin conjugates disclosed herein. A further comparison was made between the two preservatives m-cresol (formulation F3) vs. phenol (formulation F14). Formulation F14, which contains zinc and phenol, demonstrated improved stability (0.378% aggregation per Day) over formulation F3, which contains zinc and m-cresol, (0.574% aggregation per Day). This suggests that phenol is a better stabilizer as a preservative for formulations containing Compound 100.

Figure 3B:
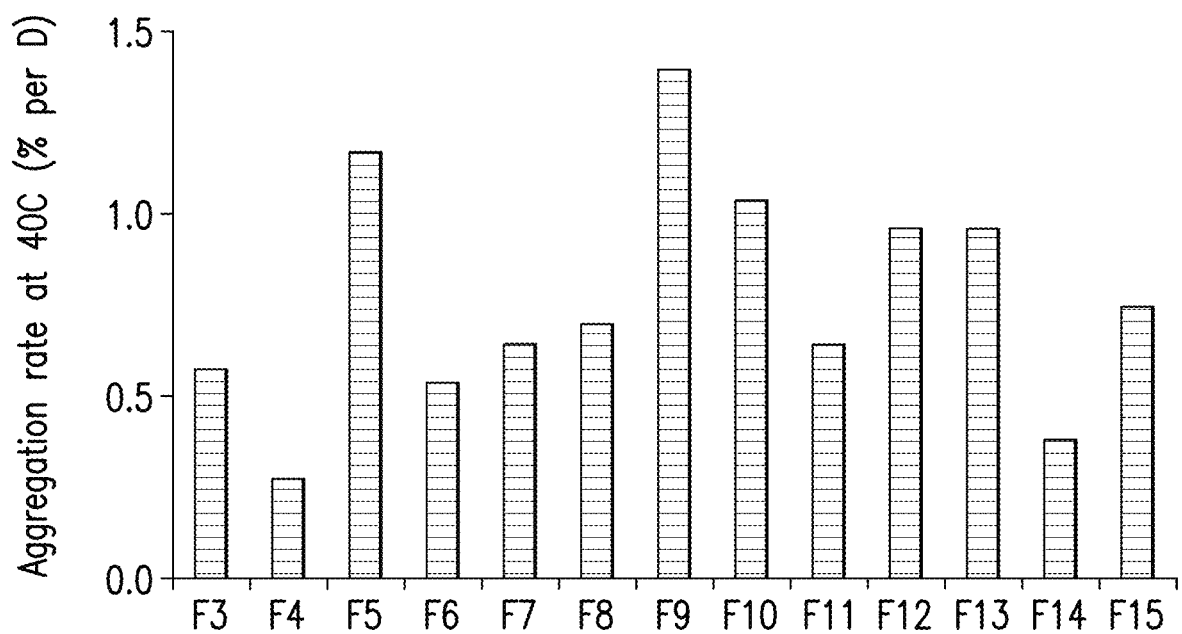

FIG. 3b represents a comparison of stability from a panel of excipients (formulations F3-F15). By comparing to formulation F3, which served as a control for this screening, formulation F4 (containing Arginine) and F14 (containing phenol) clearly stand out from the rest of excipients. Arginine slowed down the aggregation rate by 53% compared to 34% by phenol. Recombinant human serum albumin (rHSA) adversely impacted the stability of Compound 100 in formulations F5 and F9. Glycerin from two different sources also showed difference with respect to aggregation. Glycerin sourced from Hedinger (formulation F10) increased the aggregation rate by ~80% compared to that sourced from JT Baker (formulation F3).

Figure 4A:
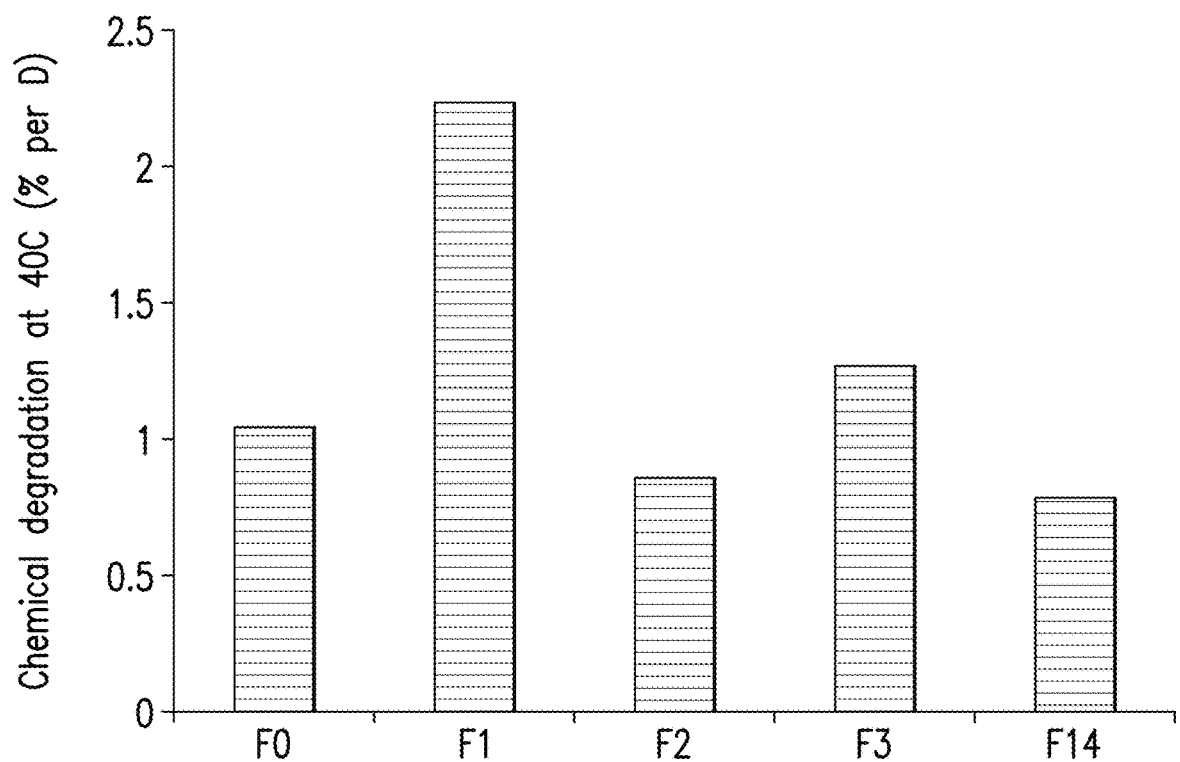
FIGS. 4a and 4b shows compound 100 stability as monitored by RP-UPLC.
Figure 4B:
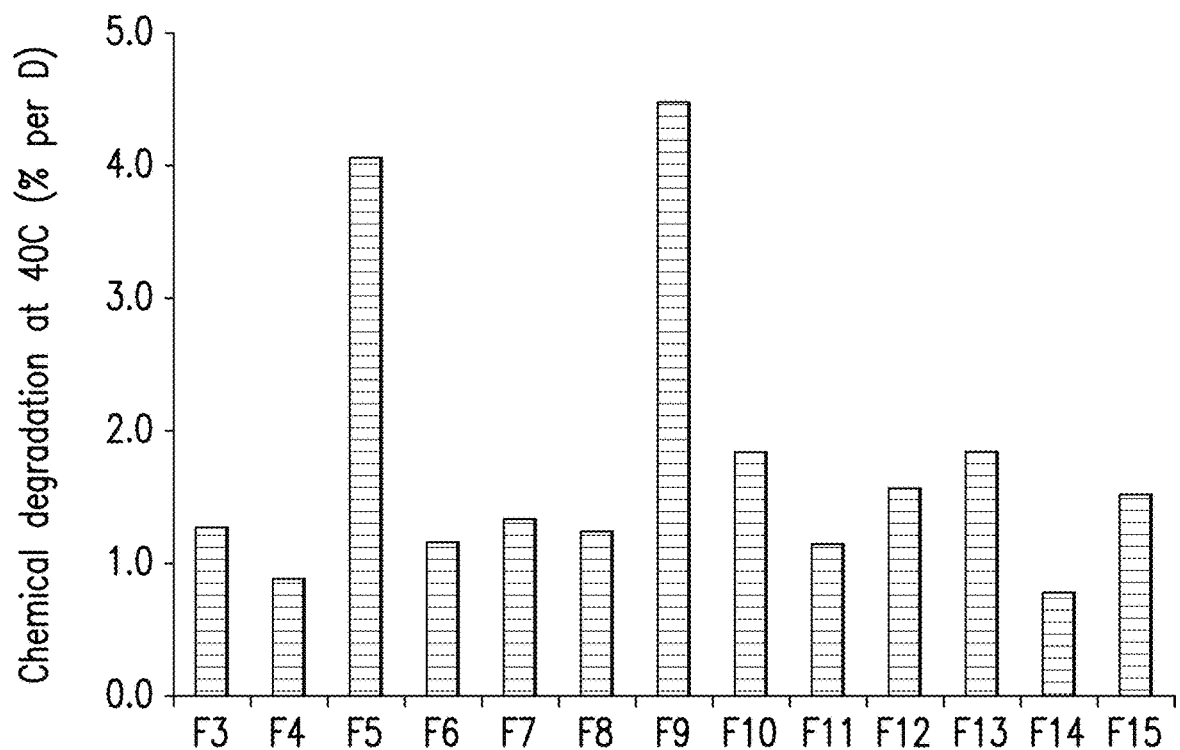

The chemical stability of Compound 100 was monitored by RP-UPLC as shown in FIGS. 4a and 4b. Arginine and phenol were again identified as stabilizers for Compound 100 with respect to chemical purity. At a high level, the trend with this assay mirrors that from size-exclusion chromatography.

Example 4

Fibril Formation

Figure 5:
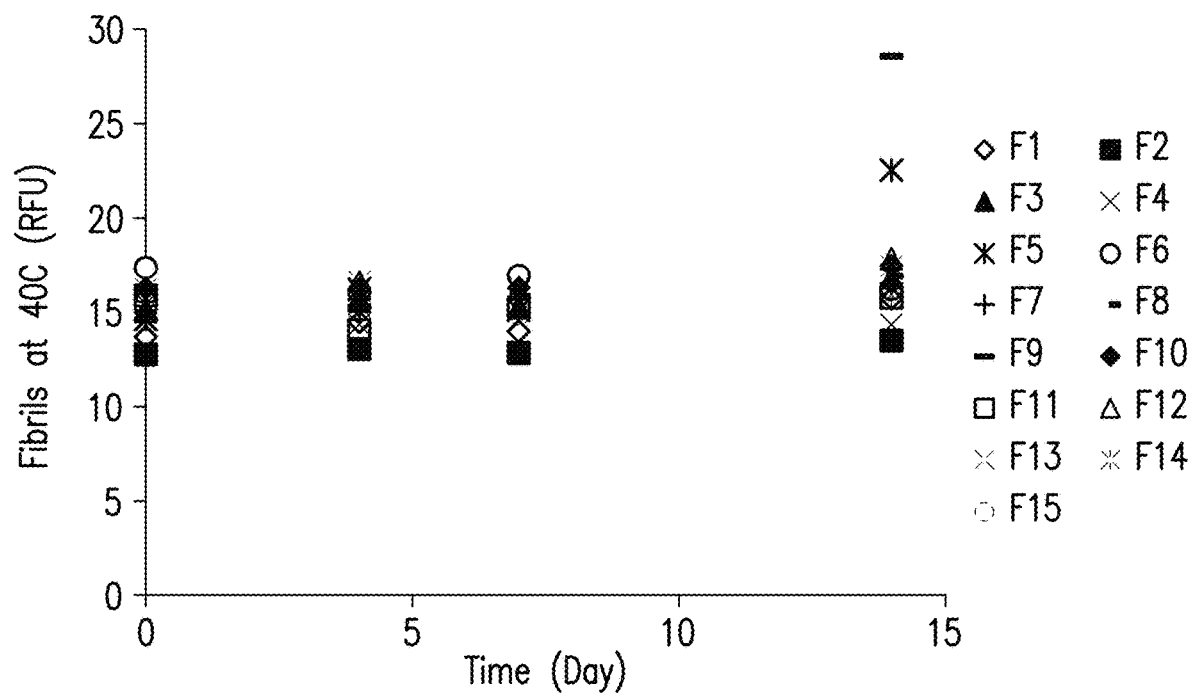
FIG. 5 shows compound 100 fibril content in various formulations under 40° C. as monitored by ThT assay. Using rHSA as an excipient leads to fibril formation of compound 100.

Insulin fibril poses significant safety risk to patients [20] and thus fibril formation was evaluated. Fibrils were measured by using a Jasco plate-based fluorometer. Samples were diluted to 0.5 mg/mL in appropriate formulated placebo and spiked with 1 mM ThT (Thioflavin T) at a final ThT concentration of 5 µM. Samples were excited at 450 nm and fluorescence emission at 482 nm was recorded. Samples were run in triplicate at 20° C. FIG. 5 monitors fibril levels of different formulations under stressed condition (40° C.). The data clearly show that only rHSA containing formulations (F5 and F9) are sensitive to fibril formation. All other formulations studied had no increase of fibril levels stored at 40° C. up to 14 days.

Example 5

Characterization of Candidate Formulations for Pharmacodynamics Studies

Based on the outcome of formulation screening, two candidate formulations (Table 1) were further evaluated in mini pigs. Phenol rather than m-cresol was used as a preservative in both formulations due to better stability. The major difference between the two candidate formulations is arginine which has been shown to stabilize Compound 100 in screening studies. The candidate formulation with arginine has to be formulated at an elevated pH of 7.2 versus 6.7 in the arginine free formulation. This is because arginine containing formulation has decreased solubility at 2-8° C. (the recommended storage temperature) at pH below 6.8 (data not shown)

TABLE 1

Candidate formulations for pharmacodynamic study in mini pigs

| Ingredient | +Arg/pH 7.2 (mg/mL) | −Arg/pH 6.7 (mg/mL) |
| --- | --- | --- |
| Compound 100 | 6.3 | 6.3 |
| Sodium Phosphate Dibasic | 1.42 | 1.42 |
| Glycerin | 16.0 | 16.0 |
| Phenol | 5.0 | 5.0 |
| L-Arginine HCl | 10.53 | — |
| Sodium Hydroxide (1N) | Adjust pH to 7.2 | Adjust pH to 6.7 |
| Hydrochloric Acid (1N) | Adjust pH to 7.2 | Adjust pH to 6.7 |

Figure 6:
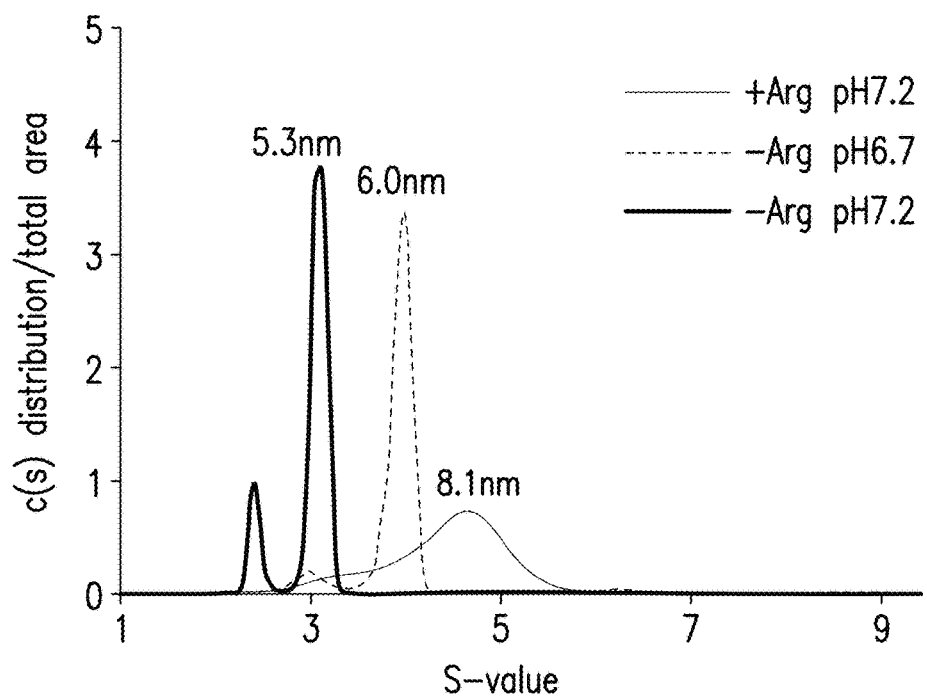
FIG. 6 shows SV-AUC distribution for candidate formulations used in mini pig study. The hydrodynamic size of each formulation was labeled above the main peak of each formulation. Using arginine as an excipient leads to a larger and broader distribution of compound 100.

Both candidate formulations were characterized by SV-AUC and DLS with the SV-AUC data shown in FIG. 6. Samples subject to SV-AUC analysis were run neat at a concentration of approximately ~6 mg/mL. The AUC cells were prepared with AUC quartz windows and meniscus matching center pieces. A Beckman-Coulter ProteorneLab XL-I AUC was used to collect interference data at 280 nm at 20° C. Scans were performed every 4 minutes for a total of 600 scans per cell at a rotation speed of 60,000 RPM. Data was analyzed using the SEDFIT software (version 13.0b) in a c(s) distribution model (sedimentation coefficient distribution). The relative percentage of each species was calculated by integration of peaks. DLS was performed as described in Example 2.

As shown in FIG. 6, the arginine free formulation (−Arg/pH6.7) shows two peaks in the c(s) distribution with the main peak at ~4 s and a smaller preceding peak at ~3 s. The Z-average hydrodynamic diameter for this formulation is 6.0 nm. In contrast, the arginine containing formulation (+Arg/pH7.2) shows much broader c(s) distribution with the peak at ~4.4 S which corresponds to a Z-average diameter of 8.1 nm by DLS. The apparent difference in size distribution among two candidate formulations may be attributed to either pH or arginine or the combination of both. For better understanding, an arginine free formulation (−Arg/pH7.2)

was prepared with pH adjusted to 7.2 and characterized by the same technique. The c(s) distribution of this formulation shows an identical pattern to the candidate formulation (−Arg/pH6.7) yet both peaks shifted towards smaller sedimentation coefficients. Corroborating with this data, the Z-average diameter of formulation (Arg/pH7.2) is 5.3 nm compared to 6.0 nm in candidate formulation (−Arg/pH6.7). Altogether, it became evident that arginine plays a major role in determining triagonist size distribution. The apparent increase of size in arginine containing formulation (+Arg/pH7.2) versus arginine free formulation (−Arg/pH6.7) is due to arginine effect not pH effect.

Example 6

Pharmacodynamic Study of Candidate Formulations in Mini Pigs

Candidate formulations were given to mini pigs (n=8) by subcutaneous administration at a dose level of 1.2 nmol/kg. The blood glucose level was monitored up to 24 hrs.

Target product profile for compound 100 requires a basal PD profile, i.e. 24-hr PD coverage, to enable a QD dosing regimen in humans. Both candidate formulations were tested in the mini pig model in order to select one with more protracted PD profile (FIG. 7), FIG. 7a shows the plasma glucose change as a function of time for both candidate formulations. Both formulations support a 24-hr coverage with the change in plasma glucose ≥100 mg/dL at 24 hr (FIG. 7b); however, formulation (+Arg/pH7.2) clearly shows a much protracted PD profile when compared to formulation (−Arg/pH6.7). The arginine containing formulation shows a trough at ~14 hr compared to 11-12 hr for the arginine free formulation.

Arginine has been used in formulations of commercial biologics such as monoclonal antibodies. Arginine plays two major roles in protein formulations: 1) stabilizer against protein aggregation, and 2) viscosity reducer for high-concentration protein formulation. In Examples 1-6, arginine was identified as a stabilizer for both physical and chemical stability. A detailed biophysical characterization by SV-AUC and DLS demonstrated the ability of arginine to modify the size distribution of compound 100 high-order structure. The formulation containing arginine has a larger and broader size distribution than the one without arginine (FIG. 6). This data further supports the observation of a protracted PD profile of the arginine containing formulation in mini pigs (FIG. 7). Protracted PD profile is likely due to a slower drug absorption in the subcutaneous space. The larger average size in the arginine formulation may slow down compound 100 diffusion which could result in slower absorption and a protracted pharmacodynamic profile. Based on both stability data from formulation screening and pharmacodynamic data from mini pigs, a zinc free formulation is proposed for clinical trials of compound 100 with the following composition: 6.3 mg/mL compound 100, 1.42 mg/mL sodium phosphate dibasic, 16.0 mg/mL glycerin, 5.0 mg/mL phenol, 10.53 mg/mL L-arginine hydrochloride, pH 7.2.

Example 7

Freeze/Thaw Study of Arginine Formulation

The arginine formulation (±Arg/pH7.2) was tested in a freeze/thaw study from −80° C. to ambient temperature up to 3 times. The freeze/thaw stress showed no impact to drug product quality as evidenced by both biochemical and potency assays (data not shown).

Example 8

Tertiary Structure Evaluation. Tertiary structure was measured by using a Jasco J-810 spectrometer. Samples were analyzed at 6 mg/mL from 240 to 350 nm, in a 0.01 cm flow cell. Formulation placebo was subtracted as the background. The following parameters were used for data collection. Bandwidth was 1 nm; accumulation was 5 per sample; and temperature was 20° C.

Figure 8A:
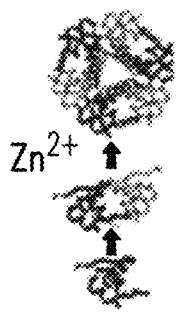
FIG. 8a-8c show the high order structure of recombinant human insulin (RHI), liraglutide and compound 100 (triagonist).

Compound 100 is a complex molecule which consists of insulin, GLP1-GIP peptide and a $C_{16}$ lipid chain conjugated to the GLP-1 peptide. Classical insulin such as regular human insulin (RHI) assembles into hexamers in the presence of zinc ion as illustrated in FIG. 8a. A zinc addition experiment was performed in order to understand whether Compound 100 follows this canonical pathway. As shown in Table 2, compound 100, in the absence of zinc, shows a sedimentation coefficient of 3.5 S. Zinc addition, however, shows no significant increase of sedimentation coefficient to 3.6 S. This is in dramatic contrast to RHI which has been well known to form hexamer in the presence of zinc. RHI monomer shows a sedimentation coefficient of 1.2 S compared to 3.1 S for RHI hexamer. It was noticed that the sedimentation coefficient of Compound 100 (regardless of zinc addition) is similar to or slightly larger than that of RHI hexamer. This clearly suggests that Compound 100 assembles into an oligomer regardless of zinc with most likely 4 to 6 monomers based on its MW of 10.4 kD.

TABLE 2

Size comparison of RHI vs. Compound 100 by SV-AUC

| Formulation | RHI (Monomer, zinc free) | RHI (Hexamer, w/zinc) | Compound 100 (zinc free) | Compound 100 (w/zinc) |
| --- | --- | --- | --- | --- |
| SV-AUC (s) | 1.2 | 3.1 | 3.5 | 3.6 |
| Theoretical MW (KD) | 5.8 | 34.8 | 10.4* | |

*Theoretical molecular weight of Compound 100 monomer

Figure 8B:
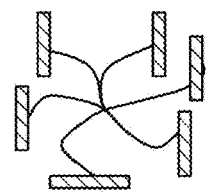
Figure 8C:
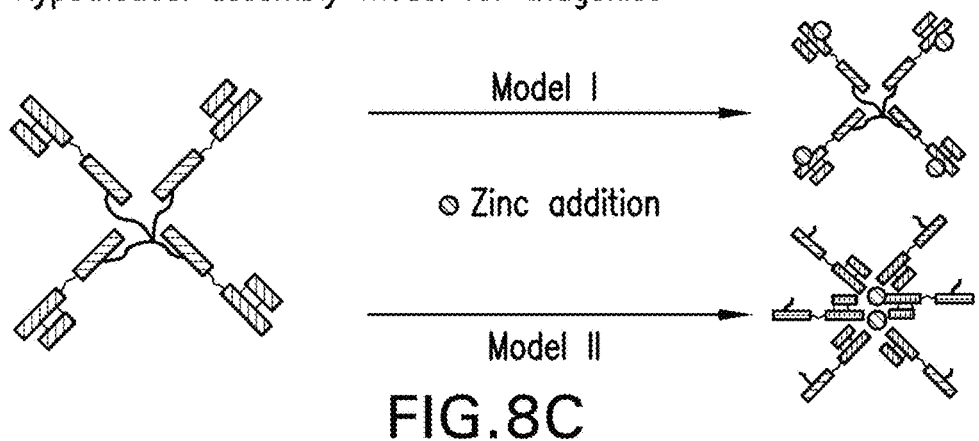

Literature data [21] suggest that liraglutide (GLP-1 analog conjugated with C16 lipid chain) forms oligomers with 6-12 monomers (FIG. 8b). In oligomers, liraglutide is believed to orient in a way that the hydrophilic portion of the peptide is exposed to the solvent while the lipid chain from different monomers is sequestered to form micelles. Oligomerization of liraglutide is a spontaneous process which does not require zinc. It was evaluated whether compound 100 oligomerization follows a similar mechanism as liraglutide. Two assembly models were proposed for compound 100 in the absence and presence of zinc as illustrated in FIG. 8c. Model I proposes that compound 100 oligomerization is independent of zinc and forms micelle-like oligomer via its lipid chain. Model II proposes that compound 100 exists as a micelle-like oligomer in the absence of zinc while it is converted to a hexamer driven by its insulin portion in the presence of zinc. It is possible that the micelle-like oligomer has similar size to the insulin-like hexamer which makes them indistinguishable by SV-AUC analysis as shown in Table 2.

Figure 9:
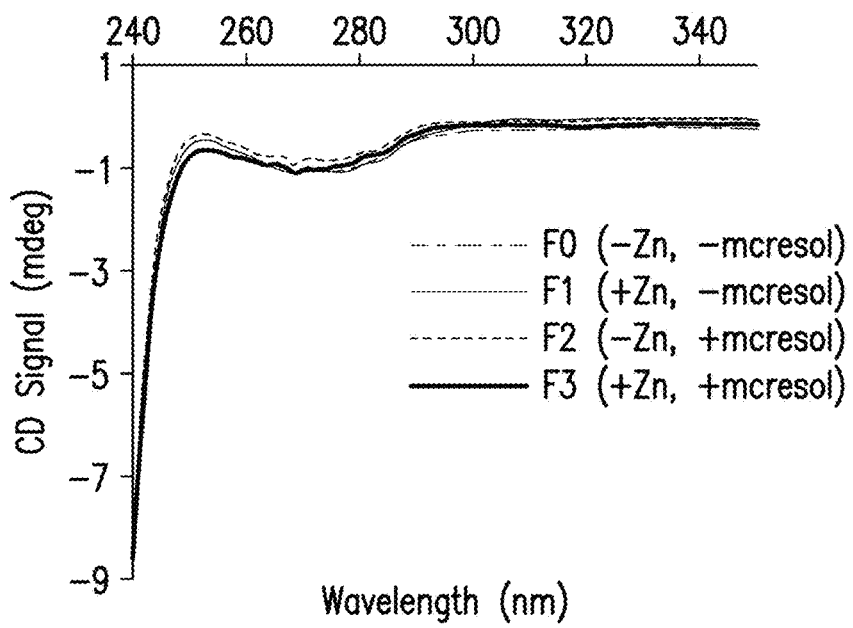
FIG. 9 shows the near-UV-CD spectra for compound 100 in different formulations. The presence of zinc and m-cresol has no impact on the high-order structure of compound 100.

To test the proposed models, compound 100 formulations were prepared with or without zinc and m-cresol. The tertiary structure of these formulations was probed by near- UV-CD measurement (FIG. 9). For model II, a dramatic change of tertiary structure should be observed as manifested by a change in near-UV-CD spectra. However, all tested formulations showed almost identical CD spectra. This suggests that model I is most likely the assembly model for compound 100 regardless of zinc presence. It is also noticed that zinc can still bind to compound 100 even though compound 100 does not form traditional zinc-insulin hexamers otherwise zinc will precipitate with phosphate buffer used in the formulation which is not the case. In contrast to the stabilization effect to classical insulin, zinc actually had adverse effect on the stability of compound 100 as demonstrated by zinc titration experiment (formulations F2, F3, and F13) in Table 3. This further confirms that compound 100 does not form insulin-like hexamers in the presence of zinc but rather oligomerizes into micelles.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

REFERENCES

1. IDF Diabetes Atlas-7$^{th}$ Edition (http://www.diabetesatlas.org/)
2. Cryer P E. 2002. Hypoglycemia: the limiting factor in the management of hyperglycaemia in type 1 and type 2 diabetes. Diabetologia 45:937-945.
3. Nathan D M, Buse J B, Davidson M B, et al. 2009. Medical management of hyperglycemia in type 2 diabetes: a consensus algorithm for the initiation and adjustment of therapy: a consensus statement of the American Diabetes Association and the European Association for the Study of Diabetes. Diabetes Care 32:193.
4. Palmer S C, Mavridis D, Nicolucci A, et al. 2016. Comparison of Clinical Outcomes and Adverse Events Associated With Glucose-Lowering Drugs in Patients with Type 2 Diabetes: A Meta-analysis. JAMA 316:313.
5. Hood T, Hovorka R. 2016. Coming of age: the artificial pancreas for type 1 diabetes. Diabetologia 59: 1795-1805.
6. Brownlee M, Cerami A. 1979. A glucose-controlled insulin-delivery system: semisynthetic insulin bound to lectin. Science 206:1190-1191.
7. Yu J, Zhang Y, Ye Y, Disanto R, Sun W, Ranson D, Ligler F S, Buse J B, Gu Z. 2015. Microneedle-array patches loaded with hypoxia-sensitive vesicles provide fast glucose-responsive insulin delivery, Proc. Natl. Acad. Sci. USA. 112:8260-8265.
8. Chou D H-C, Webber M J, Tang M J, Lin A B, Thapa L S, Deng Troung J V, Cortinas A B, Langer R, Anderson D G. 2015. Glucose-responsive insulin activity by covalent modification with aliphatic phenylboronic acid conjugates. Proc. Natl. Acad. Sci. 112:2401-2406.
9. Guo J, Sun H, Alt K, Tardy B L, Richardson J J, Suma T, Ejima H, Cui J, Hagemeyer C E, Caruso F. 2015. Boronate-phenolic network capsules with dual response to acidic pH and cis-diols. Adv. Healthc Mater. 4:1796-1801.
10. Hu J, Qian C, Lu Y, Kahkoska A R, Xie Z, Jing X, Buse J B, Gu Z. 2017. H2O2-Responsive vesicles integrated with transcutaneous patches for glucose-mediated insulin delivery. ACS Nano 11, 613-620.
11. Dimarchi R D, Mayer J P, and Smiley D L. 2016. Incretin-insulin conjugates. WO2016/049190 A1.
12. Sabine A, Natick M, Sibylle D, et al. 2010. Further Improvement in Post Prandial Glucose control with Addition of Exenatide or Sitagliptin to Combination Therapy with Insulin Glargine and Metformin. Diabetes Care 33:1509-15.
13. Gough S C L, Bode B, Woo V et al. 2014. Efficacy and safety of a fixed-ratio combination of insulin degludec and liraglutide (IDegLira) compared with its components given alone: results of a phase 3, open-label, randomised, 26-week, treat-to-target trial in insulin-naive patients with type 2 diabetes. Lancet Diabetes Endocrinol 2: 885-93.
14. B. Finan, T. Ma, N. Ottaway, T. D. Muller, K. M. Habegger, K. M. Fleppner, H et al. 2013. Unimolecular Dual Incretins Maximize Metabolic Benefits in Rodents, Monkeys, and Humans. Sci Transl Med. 5: 209ra151.
15. Lao J, Hansen B C, Dimarchi R, Pocai A. 2011 Effect of GLP1R/GCGR Dual Agonist in Monkey. Diabetes 62: A257.
16. Wedenmaier S B, Kims, Yang, G K, et al. 2010. A GIP Receptor Agonist Exhibits B-Cell Anti-Apoptotic Actions in Rat Models of Diabetes Resulting in Improved B-cell Function and Glycemic control. PLoS ONE 5: e9590.
17. Christensen M, Calanna S, Sparge-Ulrich A H, et al. 2015. Glucose-Dependent Insulinotropic Polypeptide Augments Glucagon Responses to Hypoglycemia in Type 1 Diabetes. Diabetes 64:72-78.
18. Christensen M, Calanna S, Holst J J, et al. 2014. Glucose-dependent Insulinotropic Polypeptide: Blood Glucose Stabilizing Effects in Patients With Type 2 Diabetes J Clin Endocrinol Metab 99: E418-26
19. Dunn M F. 2005. Zincligand interactions modulate assembly and stability of the insulin hexamer—a review. BioMetals 18:295-303.
20. Alam P, et al. 2017. Ascorbic acid inhibits human insulin aggregation and protects against amyloid induced cytotoxicity. Arch Biochem Biophys. 2017 621:54-62.
21. Wang Y, Lomakin A, Kanai S et al. 2015. Transformation of Oligomers of Lipidated Peptide Induced by Change in pH. Mol. Pharmaceutics 12: 411-419

TABLE 3

Formulation screening for peptide tri-agonist

| Formulation | Compound 100 (mg/mL) | Na$_2$HPO$_4$ (mM) | Glycerin (mg/mL) | M-cresol (mg/mL) | Phenol (mg/mL) | Zinc (mM) | Arg (mM) | rHSA (mg/mL) | Trehalose (mg/mL) | Met (mM) | Tris (mM) | PEG400 (mg/mL) | PG* (mg/mL) |
|---|---|---|---|---|---|---|---|---|---|---|---|---|---|
| F0 | 6.25 | 10 | 16 (JB) | 0 | 0 | 0 | 0 | 0 | 0 | 0 | 0 | 0 | 0 |
| F1 | 6.25 | 10 | 16 (JB) | 0 | 0 | 0.3 | 0 | 0 | 0 | 0 | 0 | 0 | 0 |
| F2 | 6.25 | 10 | 16 (JB) | 3.2 | 0 | 0 | 0 | 0 | 0 | 0 | 0 | 0 | 0 |
| F3 | 6.25 | 10 | 16 (JB) | 3.2 | 0 | 0.3 | 0 | 0 | 0 | 0 | 0 | 0 | 0 |
| F4 | 6.25 | 10 | 16 (JB) | 3.2 | 0 | 0.3 | 25 | 0 | 0 | 0 | 0 | 0 | 0 |
| F5 | 6.25 | 10 | 16 (JB) | 3.2 | 0 | 0.3 | 0 | 10 | 0 | 0 | 0 | 0 | 0 |

TABLE 3-continued

Formulation screening for peptide tri-agonist

| Formulation | Compound 100 (mg/mL) | Na$_2$HPO$_4$ (mM) | Glycerin (mg/mL) | M-cresol (mg/mL) | Phenol (mg/mL) | Zinc (mM) | Arg (mM) | rHSA (mg/mL) | Trehalose (mg/mL) | Met (mM) | Tris (mM) | PEG400 (mg/mL) | PG* (mg/mL) |
|---|---|---|---|---|---|---|---|---|---|---|---|---|---|
| F6  | 6.25 | 10 | 16 (JB) | 3.2 | 0 | 0.3 | 0  | 0  | 20 | 0  | 0 | 0  | 0  |
| F7  | 6.25 | 10 | 16 (JB) | 3.2 | 0 | 0.3 | 0  | 0  | 0  | 10 | 0 | 0  | 0  |
| F8  | 6.25 | 10 | 16 (JB) | 3.2 | 0 | 0.3 | 0  | 0  | 0  | 0  | 5 | 0  | 0  |
| F9  | 6.25 | 10 | 16 (JB) | 3.2 | 0 | 0.3 | 0  | 10 | 20 | 10 | 5 | 0  | 0  |
| F10 | 6.25 | 10 | 16 (HD) | 3.2 | 0 | 0.3 | 0  | 0  | 0  | 0  | 0 | 0  | 0  |
| F11 | 6.25 | 10 | 10 (JB) | 3.2 | 0 | 0.3 | 0  | 0  | 0  | 0  | 0 | 50 | 0  |
| F12 | 6.25 | 10 | 0       | 3.2 | 0 | 0.3 | 0  | 0  | 20 | 0  | 0 | 0  | 16 |
| F13 | 6.25 | 10 | 16 (JB) | 3.2 | 0 | 0.6 | 0  | 0  | 0  | 0  | 0 | 0  | 0  |
| F14 | 6.25 | 10 | 16 (JB) | 0   | 5 | 0.3 | 0  | 0  | 0  | 0  | 0 | 0  | 0  |
| F15 | 6.25 | 10 | 10 (JB) | 3.2 | 0 | 0.3 | 0  | 0  | 0  | 10 | 0 | 50 | 0  |

JB: Glycerin sourced from J T Baker,
HD: Glycerin sourced from Hedinger
*PG = propylene glycol

TABLE 4

Sequence Listing Table

| SEQ ID NO: | NAME | SEQUENCE |
|---|---|---|
| 1 | Incretin portion of formula I | X$_1$X$_2$X$_3$GX$_4$FTSDX$_5$SX$_6$YLDX$_7$X$_8$AAX$_9$X$_{10}$FVX$_{11}$WLLX$_{12}$X$_{13}$GPSSGAPPPSX$_{14}$ wherein X$_1$ is His, Tyr, or absent; X$_2$ is aminoisobutyric acid; X$_3$ is Glu or Gln; X$_4$ is Thr or Ile; X$_5$ is Tyr or Lys acylated with a C$_{16}$ to C$_{20}$ alkyl group optionally via a gamma Glu linker; X$_6$ is Ile or Arg; X$_7$ is Lys, Arg, or Glu; X$_8$ is Gln or Arg; X$_9$ is Gln or aminoisobutyric acid; X$_{10}$ is Glu or Asp; X$_{11}$ is Asn, Gln, or Ala; X$_{12}$ is Ala or Asp; X$_{13}$ is Ala or Gly; and X$_{14}$ is absent, or Lys; or Lys acylated with a C$_{16}$ to C$_{20}$ alkyl group optionally via a gamma Glu |
| 2 | A chain of human insulin | Gly Ile Val Glu Gln Cys Cys Thr Ser Ile Cys Ser Leu Tyr Gln Leu Glu Asn Tyr Cys Asn |
| 3 | B chain of human insulin | Phe Val Asn Gln His Leu Cys Gly Ser His Leu Val Glu Ala Leu Tyr Leu Val Cys Gly Glu Arg Gly Phe Phe Tyr Thr Pro Lys Thr |
| 4 | lincretin peptide of Compound 99 | YX$_2$EGTFTSDYSIYLDKQAAX$_9$EFVNWLLAGGPSSGAPPPS, wherein X$_2$ and X$_9$ are each independently aminoisobutyric acid |
| 5 | Incretin peptide of Compound 100 | YX$_2$EGTFTSDX$_5$SIYLDKQAAX$_9$EFVNWLLAGGPSSGAPPPS, wherein X$_2$ and X$_9$ are each independently aminoisobutyric acid, and X$_5$ is Lys acylated with a C$_{16}$ fatty acyl group via gamma-Glu spacer |
| 6 | Incretin peptide of Compound 101 | YX$_2$EGTFTSDYSIYLDKQAAX$_9$EFVNWLLAGGPSSGAPPPSX$_{14}$, wherein X$_2$ and X$_9$ are each independently aminoisobutyric acid, and X$_{14}$ is Lys acylated with a C$_{16}$ fatty acyl group via gamma-Glu spacer |
| 7 | Incretin peptide of Compound 102 | HX$_2$EGTFTSDX$_5$SRYLDERAAQEFVAWLLDAGPSGAPPPSK, wherein X$_2$ is aminoisobutyric acid and X$_5$ is Lys acylated with a C$_{16}$ fatty acyl group via gamma-Glu spacer |

TABLE 4-continued

Sequence Listing Table

| SEQ ID NO: | NAME | SEQUENCE |
|---|---|---|
| 8 | Incretin peptide of Compound 103 | HX$_2$QGTFTSDX$_5$SRYLDERAAQDFVQWLLDAGPSGAPPPSK, wherein X$_2$ is aminoisobutyric acid and X$_5$ is Lys acylated with a C$_{16}$ fatty acyl group via gamma-Glu spacer |
| 9 | Incretin peptide of Compound 104 | HX$_2$QGTFTSDX$_5$SRYLDERAAQDFVQWLLDGGPSGAPPPSK, wherein X$_2$ is aminoisobutyric acid and X$_5$ is Lys acylated with a C$_{16}$ fatty acyl group via gamma-Glu spacer |
| 10 | Incretin peptide of Compound 105 | HX$_2$EGTFTSDX$_5$SRYLDERAAQDFVQWLLDGGPSGAPPPSK, wherein X$_2$ is aminoisobutyric acid and X$_5$ is Lys acylated with a C$_{16}$ fatty acyl group via gamma-Glu spacer |
| 11 | Incretin peptide of Compound 106 | X$_2$EGTFTSDX$_5$SIYLDKQAAX$_9$EFVNWLLAGGPSGAPPPS, wherein X$_2$ and X$_9$ are each independently aminoisobutyric acid and X$_5$ is Lys acylated with a C$_{16}$ fatty acyl group via gamma-Glu spacer |
| 12 | Incretin peptide of Compound 99 including Cysteine of linker | YX$_2$EGTFTSDYSFYLDKQAAX$_9$EFVNWLLAGGPSSGAPPPSC, wherein X$_2$ and X$_9$ are each independently atninoisobutytic acid |
| 13 | Incretin peptide of Compound 100 including Cysteine of linker | YX$_7$EGTFTSDX$_5$SIYLDKQAAX$_9$EFVNWLLAGGPSSGAPPPSC, wherein X$_2$ and X$_9$ are each independently aminoisobutyric acid, and X$_5$ is Lys acylated with a C$_{16}$ fatty acyl group via gamma-Glu spacer |
| 14 | Incretin peptide of Compound 101 including Cysteine of linker | YX$_2$EGTFTSDYSIYLDKQAAX$_9$EFVWLLAGGPSSGAPPPSX$_{14}$C, wherein X$_2$ and X$_9$ are each independently aminoisobutyric acid, and X$_{14}$ is Lys acylated with a C$_{16}$ fatty acyl group via gamma-Glu spacer |
| 15 | Incretin peptide of Compound 102 including Cysteine of linker | HX$_2$EGTFTSDX$_5$SRYLDERAAQEFVAWLLDAGPSGAPPPSKC, wherein X$_2$ is aminoisobutyric acid and X$_5$ is Lys acylated with a C$_{16}$ fatty acyl group via gamma-Glu spacer |
| 16 | Incretin peptide of Compound 103 including Cysteine of linker | HX$_2$QGTFTSDX$_5$SRYLDERAAQDFVQWLLDAGPSGAPPPSKC, wherein X$_2$ is aminoisobutyric acid and X$_5$ is Lys acylated with a C$_{16}$ fatty acyl group via gamma-Glu spacer |
| 17 | Incretin peptide of Compound 104 including Cysteine of linker | HX$_2$QGTFTSDX$_5$SRYLDERAAQDFVQWLLDGGPSGAPPPSKC, wherein X$_2$ is aminoisobutyric acid and X$_5$ is Lys acylated with a C$_{16}$ fatty acyl group via gamma-Glu spacer |

TABLE 4-continued

Sequence Listing Table

| SEQ ID NO: | NAME | SEQUENCE |
|---|---|---|
| 18 | Incretin peptide of Compound 105 including Cysteine of linker | HX$_2$EGTFTSDX$_5$SRYLDERAAQDFVQWLLDGGPSGAPPPSKC, wherein X$_2$ is aminoisobutyric acid and X$_5$ is Lys acylated with a C$_{16}$ fatty acyl group via gamma-Glu spacer |
| 19 | Incretin peptide of Compound 106 including Cysteine of linker | X$_2$EGTFTSDX$_5$SIYLDKQAAX$_9$EFVNWLLAGGPSGAPPPSC, wherein X$_2$ and X$_6$ are each independently aminoisobutyric acid and X$_5$ is Lys acylated with a C$_{16}$ fatty acyl group via gamma-Glu spacer |
| 20 | Incretin peptide of formula I including Cysteine of linker | X$_1$X$_2$X$_3$GX$_4$FTSDX$_5$SX$_6$YLDX$_7$X$_8$AAX$_9$X$_{10}$FVX$_{11}$WLLX$_{12}$X$_{13}$GPSSGAPPPSX$_{14}$C wherein X$_1$ is His, Tyr, or absent; X$_2$ is aminoisobutyric acid; X$_3$ is Glu or Gln; X$_4$ is Thr or Ile; X$_5$ is Tyr or Lys acylated with a C$_{16}$ to C$_{20}$ alkyl group optionally via a gamma Glu linker; X$_6$ is Ile or Arg; X$_7$ is Lys, Arg, or Glu; X$_8$ is Gln or Arg; X$_9$ is Gln or aminoisobutyric acid; X$_{10}$ is Glu or Asp; X$_{11}$ is Asn, Gln, or Ala; X$_{12}$ is Ala or Asp; X$_{13}$ is Ala or Gly; and X$_{14}$ is absent, or Lys, or Lys acylated with a C$_{16}$ to C$_{20}$ alkyl group optionally via a gamma Glu |

What is claimed:

1. An aqueous pharmaceutical formulation comprising (i) a therapeutically effective amount of an incretin-insulin conjugate which comprises an incretin peptide and an insulin molecule, (ii) a buffer, (iii) glycerin, (iv) phenol or m-cresol, and (v) L-arginine HCl, wherein the pharmaceutical formulation has a pH of about 6.9-7.5;

wherein the incretin peptide has the structure:
$X_1X_2X_3GX_4FTSDX_5SX_6YLDX_7XsAAX_9X_{10}FVX_{11}WLLX_{12}X_{13}GPSSGAPPPSX_{14}$ wherein $X_1$ is His, Tyr, or absent;
$X_2$ is aminoisobutyric acid;
$X_3$ is Glu or Gln;
$X_4$ is Thr or Ile;
$X_5$ is Tyr or Lys acylated with a $C_{16}$ to $C_{20}$ alkyl group optionally via a gamma Glu linker;
$X_6$ is Ile or Arg;
$X_7$ is Lys, Arg, or Glu;
$X_8$ is Gln or Arg;
$X_9$ is Gln or aminoisobutyric acid;
$X_{10}$ is Glu or Asp;
$X_{11}$ is Asn, Gln, or Ala;
$X_{12}$ is Ala or Asp;
$X_{13}$ is Ala or Gly; and
$X_{14}$ is absent, Lys, Lys acylated with a $C_{16}$ to $C_{20}$ alkyl group optionally via a gamma Glu;

wherein the insulin molecule comprises an A chain polypeptide and a B chain polypeptide of human insulin, wherein the B chain is linked to said A chain through disulfide linkages and wherein the incretin peptide is linked to the insulin peptide via a linear chain spacer of 5 to 10 atoms, wherein the spacer comprises a disulfide linkage within the backbone of the spacer linear chain, wherein the linear chain spacer joining the incretin peptide to the insulin molecule comprises the general structure of:

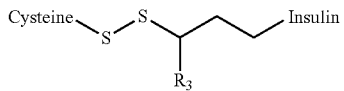

wherein $R_3$ is H or $CH_3$;

wherein the cysteine of the linear chain spacer joining the incretin peptide to the insulin molecule is at the C-terminal end of the incretin peptide;

wherein the aqueous pharmaceutical formulation comprises about 1-100 mg/mL of the incretin-insulin conjugate, about 4-6 mg/mL of m-cresol or about 5.0 mg/mL of phenol about 6.3 mg/mL of the incretin-insulin conjugate, about 16 mg/mL of glycerin, about 10 mM sodium phosphate dibasic, and about 10.53 mg/mL of L-Arginine HCl.

2. The aqueous pharmaceutical formulation of claim 1, wherein the incretin peptide is selected from the group consisting of:

(i) $YX_2EGTFTSDYSIYLDKQAAX_9EFVNWLLAGGP-SSGAPPPS$, wherein $X_2$ and $X_9$ are each independently aminoisobutyric acid (SEQ ID NO:4);

(ii) $YX_2EGTFTSDX_5SIYLDKQAAX_9EFVNWLLAGG-PSSGAPPPS$, wherein $X_2$ and $X_9$ are each independently aminoisobutyric acid, and $X_5$ is Lys acylated with a $C_{16}$ fatty acyl group via gamma-Glu spacer (SEQ ID NO:5);

(iii) $YX_2EGTFTSDYSIYLDKQAAX_9EFVNWLLAGGP-SSGAPPPSX_{14}$, wherein $X_2$ and $X_9$ are each independently aminoisobutyric acid, and $X_{14}$ is Lys acylated with a $C_{16}$ fatty acyl group via gamma-Glu spacer (SEQ ID NO:6);

(iv) $HX_2EGTFTSDXsSRYLDERAAQEFVAWLLDAGP-SGAPPPSK$, wherein $X_2$ is aminoisobutyric acid and $X_5$ is Lys acylated with a $C_{16}$ fatty acyl group via gamma-Glu spacer (SEQ ID NO:7);

(v) $HX_2QGTFTSDXsSRYLDERAAQDFVQWLLDAG-PSGAPPPSK$, wherein $X_2$ is aminoisobutyric acid and $X_5$ is Lys acylated with a $C_{16}$ fatty acyl group via gamma-Glu spacer (SEQ ID NO:8);

(vi) $HX_2QGTFTSDX_5SRYLDERAAQDFVQWLLDGG-PSGAPPPSK$, wherein $X_2$ is aminoisobutyric acid and $X_5$ is Lys acylated with a $C_{16}$ fatty acyl group via gamma-Glu spacer (SEQ ID NO:9);

(vii) $HX_2EGTFTSDXsSRYLDERAAQDFVQWLLDGG-PSGAPPPSK$, wherein $X_2$ is aminoisobutyric acid and $X_5$ is Lys acylated with a $C_{16}$ fatty acyl group via gamma-Glu spacer (SEQ ID NO:10); and (viii) $X_2EGTFTSDX_5SIYLDKQAAX_9EFVNWLLAGGP-SGAPPPS$, wherein $X_2$ and $X_9$ are each independently aminoisobutyric acid and $X_5$ is Lys acylated with a $C_{16}$ fatty acyl group via gamma-Glu spacer (SEQ ID NO:11).

3. The aqueous pharmaceutical formulation of claim 2, wherein the incretin peptide is $YX_2EGTFTSDX_5SIYLDKQAAX_9EFVNWLLAGGPSS-GAPPPS$, wherein $X_2$ and $X_9$ are each independently aminoisobutyric acid, and $X_5$ is Lys acylated with a $C_{16}$ fatty acyl group via gamma-Glu (SEQ ID NO:5).

4. The aqueous formulation of claim 1, wherein the incretin-insulin conjugate is selected from one of:

(i) $YX_2EGTFTSDYSIYLDKQAAX_9EFVNWLLAGGP-SSGAPPPSC$, wherein $X_2$ and $X_9$ are each independently aminoisobutyric acid (SEQ ID NO:12);

(ii) $YX_2EGTFTSDX_5SIYLDKQAAX_9EFVNWLLAGG-PSSGAPPPSC$, wherein $X_2$ and $X_9$ are each independently aminoisobutyric acid, and $X_5$ is Lys acylated with a $C_{16}$ fatty acyl group via gamma-Glu spacer (SEQ ID NO:13);

(iii) $YX_2EGTFTSDYSIYLDKQAAX_9EFVNWLLAGGP-SSGAPPPSX_{14}C$, wherein $X_2$ and $X_9$ are each independently aminoisobutyric acid, and $X_{14}$ is Lys acylated with a $C_{16}$ fatty acyl group via gamma-Glu spacer (SEQ ID NO:14);

(iv) HX$_2$EGTFTSDX$_5$SRYLDERAAQEFVAWLLDAGP-SGAPPPSKC, wherein $X_2$ is aminoisobutyric acid and $X_5$ is Lys acylated with a $C_{16}$ fatty acyl group via gamma-Glu spacer (SEQ ID NO:15)

(v) HX$_2$QGTFTSDXSSRYLDERAAQDFVQWLLDAG-PSGAPPPSKC, wherein $X_2$ is aminoisobutyric acid and $X_5$ is Lys acylated with a $C_{16}$ fatty acyl group via gamma-Glu spacer (SEQ ID NO:16);

(vi) HX$_2$QGTFTSDXSSRYLDERAAQDFVQWLLDGG-PSGAPPPSKC, wherein $X_2$ is aminoisobutyric acid and $X_5$ is Lys acylated with a $C_{16}$ fatty acyl group via gamma-Glu spacer (SEQ ID NO:17);

(vii) HX$_2$EGTFTSDXSSRYLDERAAQDFVQWLLDGG-PSGAPPPSKC, wherein $X_2$ is aminoisobutyric acid and $X_5$ is Lys acylated with a $C_{16}$ fatty acyl group via gamma-Glu spacer (SEQ ID NO:18); and (viii) X$_2$EGTFTSDX$_5$SIYLDKQAAX$_9$EFVNWLLAGGP-SGAPPPSC, wherein $X_2$ and $X_9$ are each independently aminoisobutyric acid and $X_5$ is Lys acylated with a $C_{16}$ fatty acyl group via gamma-Glu spacer (SEQ ID NO:19);

wherein the S group of the Cys residue of the incretin of any one of SEQ ID NO: 12-19 is conjugated to the alpha amino group of the N-terminal Phe residue of the B-chain polypeptide of an insulin heterodimer having an A-chain polypeptide of SEQ ID NO: 2 and a B-chain polypeptide of SEQ ID NO: 3 via a linker having the structure S-CH2-CH2-CH2 in a disulfide linkage.

5. The aqueous pharmaceutical formulation of claim 4, wherein the incretin-insulin conjugate is YX$_2$EGTFTSDX$_5$SIYLDKQAAX$_9$EFVNWLLAGGPSS-GAPPPSC, wherein $X_2$ and $X_9$ are each independently aminoisobutyric acid, and $X_5$ is Lys acylated with a $C_{16}$ fatty acyl group via gamma-Glu spacer (SEQ ID NO:13) and wherein the S group of the Cys residue of the incretin of any one of SEQ ID NO: 12-19 is conjugated to the alpha amino group of the N-terminal Phe residue of the B-chain polypeptide of an insulin heterodimer having an A-chain polypeptide of SEQ ID NO: 2 and a B-chain polypeptide of SEQ ID NO: 3 via a linker having the structure S-CH2-CH2-CH2 in a disulfide linkage.

6. The aqueous pharmaceutical formulation of claim 1, wherein the formulation comprises phenol.

7. The aqueous pharmaceutical formulation of claim 1, wherein the incretin-insulin conjugate is compound 99, compound 100, compound 101, compound 102, compound 103, compound 104, compound 105, or compound 106.

8. The aqueous pharmaceutical formulation of claim 7, wherein the incretin-insulin conjugate is compound 100.

9. The aqueous pharmaceutical formulation of claim 1, wherein the formulation does not contain zinc.

10. The aqueous pharmaceutical formulation of claim 1, wherein administration of the formulation results in a protracted pharmacokinetic profile as compared to an aqueous pharmaceutical formulation which does not contain L-Arginine HCl.

11. The aqueous pharmaceutical formulation of claim 1, wherein the formulation is contained in a glass vial or an injection device.

12. A method of treating a patient or individual having a metabolic disease, comprising administering to the patient or individual an effective amount of the formulation of claim 1 to treat the metabolic disease in the patient or individual.

13. The method of claim 12, wherein the metabolic disease is diabetes, non alcoholic fatty liver disease (NAFLD), non-alcoholic steatohepatitis (NASH), or obesity.

14. The method of claim 13, wherein the diabetes is Type I diabetes, Type II diabetes, or gestational diabetes.

* * * * *

SEQUENCE LISTING

<160> NUMBER OF SEQ ID NOS: 20

<210> SEQ ID NO 1
<211> LENGTH: 40
<212> TYPE: PRT
<213> ORGANISM: Artificial Sequence
<220> FEATURE:
<223> OTHER INFORMATION: Incretin portion of formula I
<220> FEATURE:
<221> NAME/KEY: MISC_FEATURE
<222> LOCATION: (1)..(1)
<223> OTHER INFORMATION: X1 is His, Tyr, or absent
<220> FEATURE:
<221> NAME/KEY: MISC_FEATURE
<222> LOCATION: (2)..(2)
<223> OTHER INFORMATION: X2 is aminoisobutyric acid
<220> FEATURE:
<221> NAME/KEY: MISC_FEATURE
<222> LOCATION: (3)..(3)
<223> OTHER INFORMATION: X3 is Glu or Gln
<220> FEATURE:
<221> NAME/KEY: MISC_FEATURE
<222> LOCATION: (5)..(5)
<223> OTHER INFORMATION: X5 is Thr or Ile
<220> FEATURE:
<221> NAME/KEY: MISC_FEATURE
<222> LOCATION: (10)..(10)
<223> OTHER INFORMATION: X10 is Tyr or Lys acylated with a C16 to C20 alkyl group optionally via a gamma Glu linker
<220> FEATURE:
<221> NAME/KEY: MISC_FEATURE

```
<222> LOCATION: (12)..(12)
<223> OTHER INFORMATION: X12 is Ile or Arg
<220> FEATURE:
<221> NAME/KEY: MISC_FEATURE
<222> LOCATION: (16)..(16)
<223> OTHER INFORMATION: X16 is Lys, Arg, or Glu
<220> FEATURE:
<221> NAME/KEY: MISC_FEATURE
<222> LOCATION: (17)..(17)
<223> OTHER INFORMATION: X17 is Gln or Arg
<220> FEATURE:
<221> NAME/KEY: MISC_FEATURE
<222> LOCATION: (20)..(20)
<223> OTHER INFORMATION: X20 is Gln or aminoisobutyric acid
<220> FEATURE:
<221> NAME/KEY: MISC_FEATURE
<222> LOCATION: (21)..(21)
<223> OTHER INFORMATION: X21 is Glu or Asp
<220> FEATURE:
<221> NAME/KEY: MISC_FEATURE
<222> LOCATION: (24)..(24)
<223> OTHER INFORMATION: X24 is Asn, Gln, or Ala
<220> FEATURE:
<221> NAME/KEY: MISC_FEATURE
<222> LOCATION: (28)..(28)
<223> OTHER INFORMATION: X28 is Ala or Asp
<220> FEATURE:
<221> NAME/KEY: MISC_FEATURE
<222> LOCATION: (29)..(29)
<223> OTHER INFORMATION: X29 is Ala or Gly
<220> FEATURE:
<221> NAME/KEY: MISC_FEATURE
<222> LOCATION: (40)..(40)
<223> OTHER INFORMATION: X40 is absent, or Lys, or Lys acylated with a
      C16 to C20 alkyl group optionally via a gamma Glu

<400> SEQUENCE: 1

Xaa Xaa Xaa Gly Xaa Phe Thr Ser Asp Xaa Ser Xaa Tyr Leu Asp Xaa
1               5                   10                  15

Xaa Ala Ala Xaa Xaa Phe Val Xaa Trp Leu Leu Xaa Xaa Gly Pro Ser
            20                  25                  30

Ser Gly Ala Pro Pro Ser Xaa
        35                  40

<210> SEQ ID NO 2
<211> LENGTH: 21
<212> TYPE: PRT
<213> ORGANISM: Homo sapiens

<400> SEQUENCE: 2

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 3
<211> LENGTH: 30
<212> TYPE: PRT
<213> ORGANISM: Homo sapiens

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 4
<211> LENGTH: 39
<212> TYPE: PRT
```

```
<213> ORGANISM: Artificial Sequence
<220> FEATURE:
<223> OTHER INFORMATION: Incretin peptide of Compound 99
<220> FEATURE:
<221> NAME/KEY: MISC_FEATURE
<222> LOCATION: (2)..(2)
<223> OTHER INFORMATION: wherein X2 and X20 are each independently
      aminoisobutyric acid
<220> FEATURE:
<221> NAME/KEY: MISC_FEATURE
<222> LOCATION: (20)..(20)
<223> OTHER INFORMATION: wherein X2 and X20 are each independently
      aminoisobutyric acid

<400> SEQUENCE: 4

Tyr Xaa Glu Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser
        35

<210> SEQ ID NO 5
<211> LENGTH: 39
<212> TYPE: PRT
<213> ORGANISM: Artificial Sequence
<220> FEATURE:
<223> OTHER INFORMATION: Incretin peptide of Compound 100
<220> FEATURE:
<221> NAME/KEY: MISC_FEATURE
<222> LOCATION: (2)..(2)
<223> OTHER INFORMATION: wherein X2 is aminoisobutyric acid
<220> FEATURE:
<221> NAME/KEY: MISC_FEATURE
<222> LOCATION: (10)..(10)
<223> OTHER INFORMATION: wherein X10 is Lys acylated with a C16 fatty
      acyl group via gamma-Glu spacer
<220> FEATURE:
<221> NAME/KEY: MISC_FEATURE
<222> LOCATION: (20)..(20)
<223> OTHER INFORMATION: wherein X20 is aminoisobutyric acid

<400> SEQUENCE: 5

Tyr Xaa Glu Gly Thr Phe Thr Ser Asp Xaa Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser
        35

<210> SEQ ID NO 6
<211> LENGTH: 40
<212> TYPE: PRT
<213> ORGANISM: Artificial Sequence
<220> FEATURE:
<223> OTHER INFORMATION: Incretin peptide of Compound 101
<220> FEATURE:
<221> NAME/KEY: MISC_FEATURE
<222> LOCATION: (2)..(2)
<223> OTHER INFORMATION: wherein X2 is aminoisobutyric acid
<220> FEATURE:
<221> NAME/KEY: MISC_FEATURE
<222> LOCATION: (20)..(20)
<223> OTHER INFORMATION: wherein X20 is aminoisobutyric acid
<220> FEATURE:
<221> NAME/KEY: MISC_FEATURE
<222> LOCATION: (40)..(40)
<223> OTHER INFORMATION: wherein X40 is Lys acylated with a C16 fatty
      acyl group via gamma-Glu spacer
```

-continued

```
<400> SEQUENCE: 6

Tyr Xaa Glu Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Xaa
        35                  40

<210> SEQ ID NO 7
<211> LENGTH: 39
<212> TYPE: PRT
<213> ORGANISM: Artificial Sequence
<220> FEATURE:
<223> OTHER INFORMATION: Incretin peptide of Compound 102
<220> FEATURE:
<221> NAME/KEY: MISC_FEATURE
<222> LOCATION: (2)..(2)
<223> OTHER INFORMATION: wherein X2 is aminoisobutyric acid
<220> FEATURE:
<221> NAME/KEY: MISC_FEATURE
<222> LOCATION: (10)..(10)
<223> OTHER INFORMATION: wherein X10 is Lys acylated with a C16 fatty
      acyl group via gamma-Glu spacer

<400> SEQUENCE: 7

His Xaa Glu Gly Thr Phe Thr Ser Asp Xaa Ser Arg Tyr Leu Asp Glu
1               5                   10                  15

Arg Ala Ala Gln Glu Phe Val Ala Trp Leu Leu Asp Ala Gly Pro Ser
            20                  25                  30

Gly Ala Pro Pro Pro Ser Lys
        35

<210> SEQ ID NO 8
<211> LENGTH: 39
<212> TYPE: PRT
<213> ORGANISM: Artificial Sequence
<220> FEATURE:
<223> OTHER INFORMATION: Incretin peptide of Compound 103
<220> FEATURE:
<221> NAME/KEY: MISC_FEATURE
<222> LOCATION: (2)..(2)
<223> OTHER INFORMATION: wherein X2 is aminoisobutyric acid
<220> FEATURE:
<221> NAME/KEY: MISC_FEATURE
<222> LOCATION: (10)..(10)
<223> OTHER INFORMATION: wherein X10 is Lys acylated with a C16 fatty
      acyl group via gamma-Glu spacer

<400> SEQUENCE: 8

His Xaa Gln Gly Thr Phe Thr Ser Asp Xaa Ser Arg Tyr Leu Asp Glu
1               5                   10                  15

Arg Ala Ala Gln Asp Phe Val Gln Trp Leu Leu Asp Ala Gly Pro Ser
            20                  25                  30

Gly Ala Pro Pro Pro Ser Lys
        35

<210> SEQ ID NO 9
<211> LENGTH: 39
<212> TYPE: PRT
<213> ORGANISM: Artificial Sequence
<220> FEATURE:
<223> OTHER INFORMATION: Incretin peptide of Compound 104
<220> FEATURE:
<221> NAME/KEY: MISC_FEATURE
<222> LOCATION: (2)..(2)
<223> OTHER INFORMATION: wherein X2 is aminoisobutyric acid
```

```
<220> FEATURE:
<221> NAME/KEY: MISC_FEATURE
<222> LOCATION: (10)..(10)
<223> OTHER INFORMATION: wherein X10 is Lys acylated with a C16 fatty
      acyl group via gamma-Glu spacer

<400> SEQUENCE: 9

His Xaa Gln Gly Thr Phe Thr Ser Asp Xaa Ser Arg Tyr Leu Asp Glu
1               5                   10                  15

Arg Ala Ala Gln Asp Phe Val Gln Trp Leu Leu Asp Gly Gly Pro Ser
            20                  25                  30

Gly Ala Pro Pro Pro Ser Lys
        35

<210> SEQ ID NO 10
<211> LENGTH: 39
<212> TYPE: PRT
<213> ORGANISM: Artificial Sequence
<220> FEATURE:
<223> OTHER INFORMATION: Incretin peptide of Compound 105
<220> FEATURE:
<221> NAME/KEY: MISC_FEATURE
<222> LOCATION: (2)..(2)
<223> OTHER INFORMATION: wherein X2 is aminoisobutyric acid
<220> FEATURE:
<221> NAME/KEY: MISC_FEATURE
<222> LOCATION: (10)..(10)
<223> OTHER INFORMATION: wherein X10 is Lys acylated with a C16 fatty
      acyl group via gamma-Glu spacer

<400> SEQUENCE: 10

His Xaa Glu Gly Thr Phe Thr Ser Asp Xaa Ser Arg Tyr Leu Asp Glu
1               5                   10                  15

Arg Ala Ala Gln Asp Phe Val Gln Trp Leu Leu Asp Gly Gly Pro Ser
            20                  25                  30

Gly Ala Pro Pro Pro Ser Lys
        35

<210> SEQ ID NO 11
<211> LENGTH: 37
<212> TYPE: PRT
<213> ORGANISM: Artificial Sequence
<220> FEATURE:
<223> OTHER INFORMATION: Incretin peptide of Compound 106
<220> FEATURE:
<221> NAME/KEY: MISC_FEATURE
<222> LOCATION: (1)..(1)
<223> OTHER INFORMATION: wherein X1 is aminoisobutyric acid
<220> FEATURE:
<221> NAME/KEY: MISC_FEATURE
<222> LOCATION: (9)..(9)
<223> OTHER INFORMATION: wherein X9 is Lys acylated with a C16 fatty
      acyl group via gamma-Glu spacer
<220> FEATURE:
<221> NAME/KEY: MISC_FEATURE
<222> LOCATION: (19)..(19)
<223> OTHER INFORMATION: wherein X19 is aminoisobutyric acid

<400> SEQUENCE: 11

Xaa Glu Gly Thr Phe Thr Ser Asp Xaa Ser Ile Tyr Leu Asp Lys Gln
1               5                   10                  15

Ala Ala Xaa Glu Phe Val Asn Trp Leu Leu Ala Gly Gly Pro Ser Gly
            20                  25                  30

Ala Pro Pro Pro Ser
        35

<210> SEQ ID NO 12
```

-continued

```
<211> LENGTH: 40
<212> TYPE: PRT
<213> ORGANISM: Artificial Sequence
<220> FEATURE:
<223> OTHER INFORMATION: Incretin peptide of Compound 99 including
      Cysteine of linker
<220> FEATURE:
<221> NAME/KEY: MISC_FEATURE
<222> LOCATION: (2)..(2)
<223> OTHER INFORMATION: wherein X2 is aminoisobutyric acid
<220> FEATURE:
<221> NAME/KEY: MISC_FEATURE
<222> LOCATION: (20)..(20)
<223> OTHER INFORMATION: wherein X20 is aminoisobutyric acid

<400> SEQUENCE: 12

Tyr Xaa Glu Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Cys
        35                  40

<210> SEQ ID NO 13
<211> LENGTH: 40
<212> TYPE: PRT
<213> ORGANISM: Artificial Sequence
<220> FEATURE:
<223> OTHER INFORMATION: Incretin peptide of Compound 100 including
      Cysteine of linker
<220> FEATURE:
<221> NAME/KEY: MISC_FEATURE
<222> LOCATION: (2)..(2)
<223> OTHER INFORMATION: wherein X2 is aminoisobutyric acid
<220> FEATURE:
<221> NAME/KEY: MISC_FEATURE
<222> LOCATION: (10)..(10)
<223> OTHER INFORMATION: wherein X10 is Lys acylated with a C16 fatty
      acyl group via gamma-Glu spacer
<220> FEATURE:
<221> NAME/KEY: MISC_FEATURE
<222> LOCATION: (20)..(20)
<223> OTHER INFORMATION: wherein X20 is aminoisobutyric acid

<400> SEQUENCE: 13

Tyr Xaa Glu Gly Thr Phe Thr Ser Asp Xaa Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Cys
        35                  40

<210> SEQ ID NO 14
<211> LENGTH: 41
<212> TYPE: PRT
<213> ORGANISM: Artificial Sequence
<220> FEATURE:
<223> OTHER INFORMATION: Incretin peptide of Compound 101 including
      Cysteine of linker
<220> FEATURE:
<221> NAME/KEY: MISC_FEATURE
<222> LOCATION: (2)..(2)
<223> OTHER INFORMATION: wherein X2 is aminoisobutyric acid
<220> FEATURE:
<221> NAME/KEY: MISC_FEATURE
<222> LOCATION: (20)..(20)
<223> OTHER INFORMATION: wherein X20 is aminoisobutyric acid
<220> FEATURE:
<221> NAME/KEY: MISC_FEATURE
<222> LOCATION: (40)..(40)
```

```
<223> OTHER INFORMATION: wherein X40 is Lys acylated with a C16 fatty
      acyl group via gamma-Glu spacer

<400> SEQUENCE: 14

Tyr Xaa Glu Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Xaa Cys
        35                  40

<210> SEQ ID NO 15
<211> LENGTH: 40
<212> TYPE: PRT
<213> ORGANISM: Artificial Sequence
<220> FEATURE:
<223> OTHER INFORMATION: Incretin peptide of Compound 102 including
      Cysteine of linker
<220> FEATURE:
<221> NAME/KEY: MISC_FEATURE
<222> LOCATION: (2)..(2)
<223> OTHER INFORMATION: wherein X2 is aminoisobutyric acid
<220> FEATURE:
<221> NAME/KEY: MISC_FEATURE
<222> LOCATION: (10)..(10)
<223> OTHER INFORMATION: wherein X10 is Lys acylated with a C16 fatty
      acyl group via gamma-Glu spacer

<400> SEQUENCE: 15

His Xaa Glu Gly Thr Phe Thr Ser Asp Xaa Ser Arg Tyr Leu Asp Glu
1               5                   10                  15

Arg Ala Ala Gln Glu Phe Val Ala Trp Leu Leu Asp Ala Gly Pro Ser
            20                  25                  30

Gly Ala Pro Pro Pro Ser Lys Cys
        35                  40

<210> SEQ ID NO 16
<211> LENGTH: 40
<212> TYPE: PRT
<213> ORGANISM: Artificial Sequence
<220> FEATURE:
<223> OTHER INFORMATION: Incretin peptide of Compound 103 including
      Cysteine of linker
<220> FEATURE:
<221> NAME/KEY: MISC_FEATURE
<222> LOCATION: (2)..(2)
<223> OTHER INFORMATION: wherein X2 is aminoisobutyric acid
<220> FEATURE:
<221> NAME/KEY: MISC_FEATURE
<222> LOCATION: (10)..(10)
<223> OTHER INFORMATION: wherein X10 is Lys acylated with a C16 fatty
      acyl group via gamma-Glu spacer

<400> SEQUENCE: 16

His Xaa Gln Gly Thr Phe Thr Ser Asp Xaa Ser Arg Tyr Leu Asp Glu
1               5                   10                  15

Arg Ala Ala Gln Asp Phe Val Gln Trp Leu Leu Asp Ala Gly Pro Ser
            20                  25                  30

Gly Ala Pro Pro Pro Ser Lys Cys
        35                  40

<210> SEQ ID NO 17
<211> LENGTH: 40
<212> TYPE: PRT
<213> ORGANISM: Artificial Sequence
```

```
<220> FEATURE:
<223> OTHER INFORMATION: Incretin peptide of Compound 104 including
      Cysteine of linker
<220> FEATURE:
<221> NAME/KEY: MISC_FEATURE
<222> LOCATION: (2)..(2)
<223> OTHER INFORMATION: wherein X2 is aminoisobutyric acid
<220> FEATURE:
<221> NAME/KEY: MISC_FEATURE
<222> LOCATION: (10)..(10)
<223> OTHER INFORMATION: wherein X10 is Lys acylated with a C16 fatty
      acyl group via gamma-Glu spacer

<400> SEQUENCE: 17

His Xaa Gln Gly Thr Phe Thr Ser Asp Xaa Ser Arg Tyr Leu Asp Glu
1               5                   10                  15

Arg Ala Ala Gln Asp Phe Val Gln Trp Leu Leu Asp Gly Gly Pro Ser
            20                  25                  30

Gly Ala Pro Pro Pro Ser Lys Cys
        35                  40

<210> SEQ ID NO 18
<211> LENGTH: 40
<212> TYPE: PRT
<213> ORGANISM: Artificial Sequence
<220> FEATURE:
<223> OTHER INFORMATION: Incretin peptide of Compound 105 including
      Cysteine of linker
<220> FEATURE:
<221> NAME/KEY: MISC_FEATURE
<222> LOCATION: (2)..(2)
<223> OTHER INFORMATION: wherein X2 is aminoisobutyric acid
<220> FEATURE:
<221> NAME/KEY: MISC_FEATURE
<222> LOCATION: (10)..(10)
<223> OTHER INFORMATION: wherein X10 is Lys acylated with a C16 fatty
      acyl group via gamma-Glu spacer

<400> SEQUENCE: 18

His Xaa Glu Gly Thr Phe Thr Ser Asp Xaa Ser Arg Tyr Leu Asp Glu
1               5                   10                  15

Arg Ala Ala Gln Asp Phe Val Gln Trp Leu Leu Asp Gly Gly Pro Ser
            20                  25                  30

Gly Ala Pro Pro Pro Ser Lys Cys
        35                  40

<210> SEQ ID NO 19
<211> LENGTH: 38
<212> TYPE: PRT
<213> ORGANISM: Artificial Sequence
<220> FEATURE:
<223> OTHER INFORMATION: Incretin peptide of Compound 106 including
      Cysteine of linker
<220> FEATURE:
<221> NAME/KEY: MISC_FEATURE
<222> LOCATION: (1)..(1)
<223> OTHER INFORMATION: wherein X1 is aminoisobutyric acid
<220> FEATURE:
<221> NAME/KEY: MISC_FEATURE
<222> LOCATION: (9)..(9)
<223> OTHER INFORMATION: wherein X9 is Lys acylated with a C16 fatty
      acyl group via gamma-Glu spacer
<220> FEATURE:
<221> NAME/KEY: MISC_FEATURE
<222> LOCATION: (19)..(19)
<223> OTHER INFORMATION: wherein X19 is aminoisobutyric acid

<400> SEQUENCE: 19

Xaa Glu Gly Thr Phe Thr Ser Asp Xaa Ser Ile Tyr Leu Asp Lys Gln
1               5                   10                  15
```

```
Ala Ala Xaa Glu Phe Val Asn Trp Leu Leu Ala Gly Gly Pro Ser Gly
            20                  25                  30

Ala Pro Pro Pro Ser Cys
        35

<210> SEQ ID NO 20
<211> LENGTH: 41
<212> TYPE: PRT
<213> ORGANISM: Artificial Sequence
<220> FEATURE:
<223> OTHER INFORMATION: Incretin peptide of formula I including
      Cysteine of linker
<220> FEATURE:
<221> NAME/KEY: MISC_FEATURE
<222> LOCATION: (1)..(1)
<223> OTHER INFORMATION: X1 is His, Tyr, or absent
<220> FEATURE:
<221> NAME/KEY: MISC_FEATURE
<222> LOCATION: (2)..(2)
<223> OTHER INFORMATION: X2 is aminoisobutyric acid
<220> FEATURE:
<221> NAME/KEY: MISC_FEATURE
<222> LOCATION: (3)..(3)
<223> OTHER INFORMATION: X3 is Glu or Gln
<220> FEATURE:
<221> NAME/KEY: MISC_FEATURE
<222> LOCATION: (5)..(5)
<223> OTHER INFORMATION: X5 is Thr or Ile
<220> FEATURE:
<221> NAME/KEY: MISC_FEATURE
<222> LOCATION: (10)..(10)
<223> OTHER INFORMATION: X10 is Tyr or Lys acylated with a C16 to C20
      alkyl group optionally via a gamma Glu linker
<220> FEATURE:
<221> NAME/KEY: MISC_FEATURE
<222> LOCATION: (12)..(12)
<223> OTHER INFORMATION: X12 is Ile or Arg
<220> FEATURE:
<221> NAME/KEY: MISC_FEATURE
<222> LOCATION: (16)..(16)
<223> OTHER INFORMATION: X16 is Lys, Arg, or Glu
<220> FEATURE:
<221> NAME/KEY: MISC_FEATURE
<222> LOCATION: (17)..(17)
<223> OTHER INFORMATION: X17 is Gln or Arg
<220> FEATURE:
<221> NAME/KEY: MISC_FEATURE
<222> LOCATION: (20)..(20)
<223> OTHER INFORMATION: X20 is Gln or aminoisobutyric acid
<220> FEATURE:
<221> NAME/KEY: MISC_FEATURE
<222> LOCATION: (21)..(21)
<223> OTHER INFORMATION: X21 is Glu or Asp
<220> FEATURE:
<221> NAME/KEY: MISC_FEATURE
<222> LOCATION: (24)..(24)
<223> OTHER INFORMATION: X24 is Asn, Gln, or Ala
<220> FEATURE:
<221> NAME/KEY: MISC_FEATURE
<222> LOCATION: (28)..(28)
<223> OTHER INFORMATION: X28 is Ala or Asp
<220> FEATURE:
<221> NAME/KEY: MISC_FEATURE
<222> LOCATION: (29)..(29)
<223> OTHER INFORMATION: X29 is Ala or Gly
<220> FEATURE:
<221> NAME/KEY: MISC_FEATURE
<222> LOCATION: (40)..(40)
<223> OTHER INFORMATION: X40 is absent, or Lys, or Lys acylated with a
      C16 to C20 alkyl group optionally via a gamma Glu

<400> SEQUENCE: 20

Xaa Xaa Xaa Gly Xaa Phe Thr Ser Asp Xaa Ser Xaa Tyr Leu Asp Xaa
1               5                   10                  15
```

-continued

```
Xaa Ala Ala Xaa Xaa Phe Val Xaa Trp Leu Leu Xaa Xaa Gly Pro Ser
            20              25                  30

Ser Gly Ala Pro Pro Pro Ser Xaa Cys
    35                  40
```